US012751717B2

(12) United States Patent
Inouye

(10) Patent No.: US 12,751,717 B2
(45) Date of Patent: Oct. 6, 2026

(54) TWISTED TIP SOFT TISSUE ANCHORS

(71) Applicant: BOSTON SCIENTIFIC SCIMED, INC., Maple Grove, MN (US)

(72) Inventor: Joshua Mark Inouye, Brooklyn Park, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 943 days.

(21) Appl. No.: 17/981,631

(22) Filed: Nov. 7, 2022

(65) Prior Publication Data

US 2023/0142374 A1 May 11, 2023

Related U.S. Application Data

(60) Provisional application No. 63/277,406, filed on Nov. 9, 2021.

(51) Int. Cl.
*A61B 17/12* (2006.01)
*A61B 17/00* (2006.01)

(52) U.S. Cl.
CPC .. *A61B 17/12159* (2013.01); *A61B 17/12122* (2013.01); *A61B 2017/00579* (2013.01)

(58) Field of Classification Search
CPC ........ A61B 17/12177; A61B 17/12122; A61B 17/12172; A61B 17/12159; A61B 2017/00579
See application file for complete search history.

(56) References Cited

U.S. PATENT DOCUMENTS 178,283 A 6/1876 French
1,967,318 A 7/1934 Monahan
(Continued)

FOREIGN PATENT DOCUMENTS

CN 1399571 A 2/2003
CN 202143640 U 2/2012
(Continued)

OTHER PUBLICATIONS

International Search Report and Written Opinion dated Feb. 23, 2023 for International Application No. PCT/US2022/049080.
(Continued)

*Primary Examiner* — Katherine H Schwiker
(74) *Attorney, Agent, or Firm* — Seager, Tufte & Wickhem LLP

(57) ABSTRACT

An occlusive implant may include an expandable framework configured to shift between a collapsed configuration and an expanded configuration. The expandable framework includes a plurality of anchor members extending radially outward from the expandable framework in the expanded configuration, each anchor member including at least one base portion fixedly secured to the expandable framework and a plurality of anchor tips extending from each base portion. Each base portion extends longitudinally along the expandable framework. A method of making the occlusive implant may include forming the expandable framework, forming the plurality of anchor members, and fixedly attaching each base portion to the expandable framework such that each anchor member extends radially outward from the expandable framework in the expanded configuration and each base portion extends longitudinally along the expandable framework.

8 Claims, 13 Drawing Sheets

(56) References Cited

U.S. PATENT DOCUMENTS

| | | | |
|---|---|---|---|
| 3,402,710 | A | 9/1968 | Paleschuck |
| 3,540,431 | A | 11/1970 | Mobin-Uddin |
| 3,557,794 | A | 1/1971 | Van Patten |
| 3,638,652 | A | 2/1972 | Kelley |
| 3,811,449 | A | 5/1974 | Gravlee et al. |
| 3,844,302 | A | 10/1974 | Klein |
| 3,874,388 | A | 4/1975 | King et al. |
| 4,007,743 | A | 2/1977 | Blake |
| 4,108,420 | A | 8/1978 | West et al. |
| 4,175,545 | A | 11/1979 | Termanini |
| 4,309,776 | A | 1/1982 | Berguer |
| 4,341,218 | A | 7/1982 | Ü |
| 4,364,392 | A | 12/1982 | Strother et al. |
| 4,425,908 | A | 1/1984 | Simon |
| 4,545,367 | A | 10/1985 | Tucci |
| 4,585,000 | A | 4/1986 | Hershenson |
| 4,603,693 | A | 8/1986 | Conta et al. |
| 4,611,594 | A | 9/1986 | Grayhack et al. |
| 4,619,246 | A | 10/1986 | Molgaard-Nielsen et al. |
| 4,638,803 | A | 1/1987 | Rand et al. |
| 4,665,906 | A | 5/1987 | Jervis |
| 4,681,588 | A | 7/1987 | Ketharanathan et al. |
| 4,710,192 | A | 12/1987 | Liotta et al. |
| 4,718,417 | A | 1/1988 | Kittrell et al. |
| 4,759,348 | A | 7/1988 | Cawood et al. |
| 4,781,177 | A | 11/1988 | Lebigot |
| 4,793,348 | A | 12/1988 | Palmaz |
| 4,827,907 | A | 5/1989 | Tashiro |
| 4,832,055 | A | 5/1989 | Palestrant |
| 4,873,978 | A | 10/1989 | Ginsburg |
| 4,917,089 | A | 4/1990 | Sideris |
| 4,921,484 | A | 5/1990 | Hillstead |
| 4,960,412 | A | 10/1990 | Fink |
| 4,966,150 | A | 10/1990 | Etienne et al. |
| 4,998,972 | A | 3/1991 | Chin et al. |
| 5,037,810 | A | 8/1991 | Saliba, Jr. |
| 5,041,090 | A | 8/1991 | Scheglov et al. |
| 5,041,093 | A | 8/1991 | Chu |
| 5,042,707 | A | 8/1991 | Taheri |
| 5,053,009 | A | 10/1991 | Herzberg |
| 5,064,435 | A | 11/1991 | Porter |
| 5,071,407 | A | 12/1991 | Termin et al. |
| 5,078,736 | A | 1/1992 | Behl |
| 5,098,440 | A | 3/1992 | Hillstead |
| 5,108,418 | A | 4/1992 | Lefebvre |
| 5,108,420 | A | 4/1992 | Marks |
| 5,108,474 | A | 4/1992 | Riedy et al. |
| 5,116,360 | A | 5/1992 | Pinchuk et al. |
| 5,122,136 | A | 6/1992 | Guglielmi et al. |
| 5,133,733 | A | 7/1992 | Rasmussen et al. |
| 5,171,259 | A | 12/1992 | Inoue |
| 5,171,383 | A | 12/1992 | Sagaye et al. |
| 5,176,692 | A | 1/1993 | Wilk et al. |
| 5,192,301 | A | 3/1993 | Kamiya et al. |
| 5,211,658 | A | 5/1993 | Clouse |
| 5,234,458 | A | 8/1993 | Metais |
| 5,242,462 | A | 9/1993 | El-Nounnou et al. |
| 5,256,146 | A | 10/1993 | Ensminger et al. |
| 5,258,000 | A | 11/1993 | Gianturco |
| 5,258,042 | A | 11/1993 | Mehta |
| 5,279,539 | A | 1/1994 | Bohan et al. |
| 5,284,488 | A | 2/1994 | Sideris |
| 5,304,184 | A | 4/1994 | Hathaway et al. |
| 5,306,234 | A | 4/1994 | Johnson |
| 5,312,341 | A | 5/1994 | Turi |
| 5,329,942 | A | 7/1994 | Gunther et al. |
| 5,334,217 | A | 8/1994 | Das |
| 5,344,439 | A | 9/1994 | Otten |
| 5,350,398 | A | 9/1994 | Pavcnik et al. |
| 5,350,399 | A | 9/1994 | Erlebacher et al. |
| 5,353,784 | A | 10/1994 | Nady-Mohamed |
| 5,366,460 | A | 11/1994 | Eberbach |
| 5,366,504 | A | 11/1994 | Andersen et al. |
| 5,370,657 | A | 12/1994 | Irie |
| 5,375,612 | A | 12/1994 | Cottenceau et al. |
| 5,397,331 | A | 3/1995 | Himpens et al. |
| 5,397,355 | A | 3/1995 | Marin et al. |
| 5,409,444 | A | 4/1995 | Kensey et al. |
| 5,417,699 | A | 5/1995 | Klein et al. |
| 5,421,832 | A | 6/1995 | Lefebvre |
| 5,425,744 | A | 6/1995 | Fagan et al. |
| 5,427,119 | A | 6/1995 | Swartz et al. |
| 5,433,727 | A | 7/1995 | Sideris |
| 5,443,454 | A | 8/1995 | Tanabe et al. |
| 5,443,478 | A | 8/1995 | Purdy et al. |
| 5,451,235 | A | 9/1995 | Lock et al. |
| 5,454,365 | A | 10/1995 | Bonutti |
| 5,464,408 | A | 11/1995 | Duc |
| 5,469,867 | A | 11/1995 | Schmitt |
| 5,490,856 | A | 2/1996 | Person et al. |
| 5,497,774 | A | 3/1996 | Swartz et al. |
| 5,499,975 | A | 3/1996 | Cope et al. |
| 5,499,995 | A | 3/1996 | Teirstein |
| 5,522,790 | A | 6/1996 | Moll et al. |
| 5,522,822 | A | 6/1996 | Phelps et al. |
| 5,522,836 | A | 6/1996 | Palermo |
| 5,527,322 | A | 6/1996 | Klein et al. |
| 5,527,338 | A | 6/1996 | Purdy |
| 5,558,093 | A | 9/1996 | Pomeranz et al. |
| 5,558,652 | A | 9/1996 | Henke |
| 5,569,204 | A | 10/1996 | Cramer et al. |
| 5,591,196 | A | 1/1997 | Marin et al. |
| 5,614,204 | A | 3/1997 | Cochrum |
| 5,634,936 | A | 6/1997 | Linden et al. |
| 5,634,942 | A | 6/1997 | Chevillon et al. |
| 5,637,097 | A | 6/1997 | Yoon |
| 5,643,282 | A | 7/1997 | Kieturakis |
| 5,643,292 | A | 7/1997 | Hart |
| 5,649,953 | A | 7/1997 | Lefebvre |
| 5,653,690 | A | 8/1997 | Booth et al. |
| 5,662,671 | A | 9/1997 | Barbut et al. |
| 5,669,933 | A | 9/1997 | Simon et al. |
| 5,681,345 | A | 10/1997 | Euteneuer |
| 5,681,347 | A | 10/1997 | Cathcart et al. |
| 5,683,411 | A | 11/1997 | Kavteladze et al. |
| 5,690,671 | A | 11/1997 | McGurk et al. |
| 5,693,067 | A | 12/1997 | Purdy |
| 5,695,525 | A | 12/1997 | Mulhauser et al. |
| 5,700,285 | A | 12/1997 | Myers et al. |
| 5,702,421 | A | 12/1997 | Schneidt |
| 5,704,910 | A | 1/1998 | Humes |
| 5,709,224 | A | 1/1998 | Behl et al. |
| 5,709,704 | A | 1/1998 | Nott et al. |
| 5,709,707 | A | 1/1998 | Lock et al. |
| 5,722,400 | A | 3/1998 | Ockuly et al. |
| 5,724,975 | A | 3/1998 | Negus et al. |
| 5,725,512 | A | 3/1998 | Swartz et al. |
| 5,725,552 | A | 3/1998 | Kotula et al. |
| 5,725,568 | A | 3/1998 | Hastings |
| 5,733,294 | A | 3/1998 | Forber et al. |
| 5,733,302 | A | 3/1998 | Myler et al. |
| 5,735,290 | A | 4/1998 | Sterman et al. |
| 5,749,880 | A | 5/1998 | Banas et al. |
| 5,749,883 | A | 5/1998 | Halpern |
| 5,749,894 | A | 5/1998 | Engelson |
| 5,766,219 | A | 6/1998 | Horton |
| 5,766,246 | A | 6/1998 | Mulhauser et al. |
| 5,769,816 | A | 6/1998 | Barbut et al. |
| 5,776,097 | A | 7/1998 | Massoud |
| 5,776,162 | A | 7/1998 | Kleshinski |
| 5,782,860 | A | 7/1998 | Epstein et al. |
| 5,785,679 | A | 7/1998 | Abolfathi et al. |
| 5,800,454 | A | 9/1998 | Jacobsen et al. |
| 5,800,457 | A | 9/1998 | Gelbfish |
| 5,800,512 | A | 9/1998 | Letnz et al. |
| 5,807,261 | A | 9/1998 | Benaron et al. |
| 5,810,874 | A | 9/1998 | Lefebvre |
| 5,814,028 | A | 9/1998 | Swartz et al. |
| 5,814,029 | A | 9/1998 | Hassett |
| 5,814,064 | A | 9/1998 | Daniel |
| 5,820,591 | A | 10/1998 | Thompson et al. |
| 5,823,198 | A | 10/1998 | Jones et al. |
| 5,830,228 | A | 11/1998 | Knapp et al. |
| 5,833,673 | A | 11/1998 | Ockuly et al. |

(56) References Cited

U.S. PATENT DOCUMENTS 5,836,913 A 11/1998 Orth et al.
5,836,968 A 11/1998 Simon et al.
5,840,027 A 11/1998 Swartz et al.
5,843,118 A 12/1998 Sepetka et al.
5,846,260 A 12/1998 Maahs
5,846,261 A 12/1998 Kotula et al.
5,848,969 A 12/1998 Panescu et al.
5,849,005 A 12/1998 Garrison et al.
5,851,232 A 12/1998 Lois
5,853,422 A 12/1998 Huebsch et al.
5,855,597 A 1/1999 Jayaraman
5,865,791 A 2/1999 Whayne et al.
5,865,802 A 2/1999 Yoon et al.
5,868,702 A 2/1999 Stevens et al.
5,868,708 A 2/1999 Hart et al.
5,876,367 A 3/1999 Kaganov et al.
5,879,296 A 3/1999 Ockuly et al.
5,879,366 A 3/1999 Shaw et al.
5,882,340 A 3/1999 Yoon
5,885,258 A 3/1999 Sachdeva et al.
5,891,558 A 4/1999 Bell et al.
5,895,399 A 4/1999 Barbut et al.
5,902,289 A 5/1999 Swartz et al.
5,904,680 A 5/1999 Kordis et al.
5,904,703 A 5/1999 Gilson
5,906,207 A 5/1999 Shen
5,910,154 A 6/1999 Tsugita et al.
5,911,734 A 6/1999 Tsugita et al.
5,916,236 A 6/1999 Muijs Van de Moer et al.
5,925,060 A 7/1999 Forber
5,925,063 A 7/1999 Khosravi
5,925,074 A 7/1999 Gingras et al.
5,925,075 A 7/1999 Myers et al.
5,928,192 A 7/1999 Maahs
5,928,260 A 7/1999 Chin et al.
5,931,818 A 8/1999 Werp et al.
5,935,145 A 8/1999 Villar et al.
5,935,147 A 8/1999 Kensey et al.
5,935,148 A 8/1999 Villar et al.
5,941,249 A 8/1999 Maynard
5,941,896 A 8/1999 Kerr
5,944,738 A 8/1999 Amplatz et al.
5,947,997 A 9/1999 Pavcnik et al.
5,951,589 A 9/1999 Epstein et al.
5,951,599 A 9/1999 McCrory
5,954,694 A 9/1999 Sunseri
5,954,767 A 9/1999 Pajotin et al.
5,957,940 A 9/1999 Tanner et al.
5,961,545 A 10/1999 Lentz et al.
5,976,174 A 11/1999 Ruiz
5,980,514 A 11/1999 Kupiecki et al.
5,980,555 A 11/1999 Barbut et al.
5,989,281 A 11/1999 Barbut et al.
5,993,469 A 11/1999 McKenzie et al.
5,993,483 A 11/1999 Gianotti
5,997,557 A 12/1999 Barbut et al.
6,004,280 A 12/1999 Buck et al.
6,004,348 A 12/1999 Banas et al.
6,007,523 A 12/1999 Mangosong
6,007,557 A 12/1999 Ambrisco et al.
6,010,517 A 1/2000 Baccaro
6,010,522 A 1/2000 Barbut et al.
6,013,093 A 1/2000 Nott et al.
6,024,751 A 2/2000 Lovato et al.
6,024,754 A 2/2000 Engelson
6,024,755 A 2/2000 Addis
6,024,756 A 2/2000 Huebsch et al.
6,027,520 A 2/2000 Tsugita et al.
6,033,420 A 3/2000 Hahnen
6,036,720 A 3/2000 Abrams et al.
6,042,598 A 3/2000 Tsugita et al.
6,048,331 A 4/2000 Tsugita et al.
6,051,014 A 4/2000 Jang
6,051,015 A 4/2000 Maahs
6,056,720 A 5/2000 Morse
6,063,070 A 5/2000 Eder
6,063,113 A 5/2000 Kavteladze et al.
6,066,126 A 5/2000 Li et al.
6,068,621 A 5/2000 Balceta et al.
6,074,357 A 6/2000 Kaganov et al.
6,076,012 A 6/2000 Swanson et al.
6,079,414 A 6/2000 Roth
6,080,182 A 6/2000 Shaw et al.
6,080,183 A 6/2000 Tsugita et al.
6,083,239 A 7/2000 Addis
6,090,084 A 7/2000 Hassett et al.
6,096,052 A 8/2000 Callister et al.
6,096,053 A 8/2000 Bates et al.
6,110,243 A 8/2000 Wnenchak et al.
6,123,715 A 9/2000 Amplatz
6,124,523 A 9/2000 Banas et al.
6,132,438 A 10/2000 Fleischman et al.
6,135,991 A 10/2000 Muni et al.
6,136,016 A 10/2000 Barbut et al.
6,139,527 A 10/2000 Laufer et al.
6,139,573 A 10/2000 Sogard et al.
6,152,144 A 11/2000 Lesh et al.
6,152,946 A 11/2000 Broome et al.
6,156,055 A 12/2000 Ravenscroft
6,159,195 A 12/2000 Ha et al.
6,161,543 A 12/2000 Cox et al.
6,168,615 B1 1/2001 Ken et al.
6,171,329 B1 1/2001 Shaw et al.
6,179,859 B1 1/2001 Bates et al.
6,193,739 B1 2/2001 Chevillon et al.
6,203,531 B1 3/2001 Ockuly et al.
6,206,907 B1 3/2001 Marino et al.
6,214,029 B1 4/2001 Thill et al.
6,221,092 B1 4/2001 Koike et al.
6,231,561 B1 5/2001 Frazier et al.
6,231,581 B1 * 5/2001 Shank .................. A61B 17/064 606/157
6,231,589 B1 5/2001 Wessman et al.
6,235,045 B1 5/2001 Barbut et al.
6,245,012 B1 6/2001 Kleshinski
6,251,122 B1 6/2001 Tsukernik
6,258,115 B1 7/2001 Dubrul
6,267,772 B1 7/2001 Mulhauser et al.
6,267,776 B1 7/2001 O'Connell
6,270,490 B1 8/2001 Hahnen
6,270,530 B1 8/2001 Eldridge et al.
6,270,902 B1 8/2001 Tedeschi et al.
6,277,138 B1 8/2001 Levinson et al.
6,285,898 B1 9/2001 Ben-Haim
6,290,674 B1 9/2001 Roue et al.
6,290,708 B1 9/2001 Kugel et al.
6,312,407 B1 11/2001 Zadno-Azizi et al.
6,319,251 B1 11/2001 Tu et al.
6,328,727 B1 12/2001 Frazier et al.
6,328,755 B1 12/2001 Marshall
6,342,062 B1 1/2002 Suon et al.
6,346,116 B1 2/2002 Brooks et al.
6,346,895 B1 2/2002 Lee et al.
6,361,545 B1 3/2002 Macoviak et al.
6,364,895 B1 4/2002 Greenhalgh
6,368,338 B1 4/2002 Konya et al.
6,371,971 B1 4/2002 Tsugita et al.
6,375,670 B1 4/2002 Greenhalgh
6,391,044 B1 5/2002 Yadav et al.
6,398,803 B1 6/2002 Layne et al.
6,402,746 B1 6/2002 Whayne et al.
6,402,771 B1 6/2002 Palmer et al.
6,402,779 B1 6/2002 Colone et al.
6,419,669 B1 7/2002 Frazier et al.
6,440,152 B1 8/2002 Gainor et al.
6,443,972 B1 9/2002 Bosma et al.
6,447,530 B1 9/2002 Ostrovsky et al.
6,454,775 B1 9/2002 Demarais et al.
6,458,145 B1 10/2002 Ravenscroft et al.
6,464,712 B1 10/2002 Epstein et al.
6,468,291 B2 10/2002 Bates et al.
6,468,301 B1 10/2002 Amplatz et al.
6,485,501 B1 11/2002 Green
6,488,689 B1 12/2002 Kaplan et al.

(56) References Cited

U.S. PATENT DOCUMENTS

| | | | | |
|---|---|---|---|---|
| 6,511,496 | B1 | 1/2003 | Huter et al. | |
| 6,514,280 | B1 | 2/2003 | Gilson | |
| 6,517,573 | B1 | 2/2003 | Pollock et al. | |
| 6,533,782 | B2 | 3/2003 | Howell et al. | |
| 6,547,760 | B1 | 4/2003 | Samson et al. | |
| 6,547,815 | B2 | 4/2003 | Myers | |
| 6,551,303 | B1 | 4/2003 | Van Tassel et al. | |
| 6,551,344 | B2 | 4/2003 | Thill | |
| 6,558,401 | B1 | 5/2003 | Azizi | |
| 6,558,405 | B1 | 5/2003 | McInnes | |
| 6,558,414 | B2 | 5/2003 | Layne | |
| 6,562,058 | B2 | 5/2003 | Seguin et al. | |
| 6,569,184 | B2 | 5/2003 | Huter | |
| 6,569,214 | B2 | 5/2003 | Williams et al. | |
| 6,589,214 | B2 | 7/2003 | McGuckin et al. | |
| 6,589,251 | B2 | 7/2003 | Yee et al. | |
| 6,599,308 | B2 | 7/2003 | Amplatz | |
| 6,602,271 | B2 | 8/2003 | Adams et al. | |
| 6,623,508 | B2 | 9/2003 | Shaw et al. | |
| 6,641,564 | B1 | 11/2003 | Kraus | |
| 6,650,923 | B1 | 11/2003 | Lesh et al. | |
| 6,652,555 | B1 | 11/2003 | VanTassel et al. | |
| 6,652,556 | B1 | 11/2003 | VanTassel et al. | |
| 6,666,861 | B1 | 12/2003 | Grabek | |
| 6,689,150 | B1 | 2/2004 | Vantassel et al. | |
| 6,699,260 | B2 | 3/2004 | Dubrul et al. | |
| 6,699,276 | B2 | 3/2004 | Sogard et al. | |
| 6,702,825 | B2 | 3/2004 | Frazier et al. | |
| 6,712,836 | B1 | 3/2004 | Berg et al. | |
| 6,726,701 | B2 | 4/2004 | Gilson et al. | |
| 6,730,108 | B2 | 5/2004 | Van Tassel et al. | |
| 6,755,812 | B2 | 6/2004 | Peterson et al. | |
| 6,827,737 | B2 | 12/2004 | Hill et al. | |
| 6,837,901 | B2 | 1/2005 | Rabkin et al. | |
| 6,855,153 | B2 | 2/2005 | Saadat | |
| 6,911,037 | B2 | 6/2005 | Gainor et al. | |
| 6,932,838 | B2 | 8/2005 | Schwartz et al. | |
| 6,942,653 | B2 | 9/2005 | Quinn | |
| 6,949,113 | B2 | 9/2005 | Van Tassel et al. | |
| 6,958,061 | B2 | 10/2005 | Truckai et al. | |
| 6,994,092 | B2 | 2/2006 | van der Burg et al. | |
| 7,011,671 | B2 | 3/2006 | Welch | |
| 7,014,645 | B2 | 3/2006 | Greene, Jr. et al. | |
| 7,037,321 | B2 | 5/2006 | Sachdeva et al. | |
| 7,044,134 | B2 | 5/2006 | Khairkhahan et al. | |
| 7,097,651 | B2 | 8/2006 | Harrison et al. | |
| 7,128,073 | B1 | 10/2006 | van der Burg et al. | |
| 7,152,605 | B2 | 12/2006 | Khairkhahan et al. | |
| 7,169,164 | B2 | 1/2007 | Borillo et al. | |
| 7,179,275 | B2 | 2/2007 | McGuckin, Jr. et al. | |
| 7,226,466 | B2 | 6/2007 | Opolski | |
| 7,303,526 | B2 | 12/2007 | Sharkey et al. | |
| 7,323,002 | B2 | 1/2008 | Johnson et al. | |
| 7,597,704 | B2 | 10/2009 | Frazier et al. | |
| 7,678,123 | B2 | 3/2010 | Chanduszko | |
| 7,695,425 | B2 | 4/2010 | Schweich et al. | |
| 7,713,282 | B2 | 5/2010 | Frazier et al. | |
| 7,722,641 | B2 | 5/2010 | van der Burg et al. | |
| 7,727,189 | B2 | 6/2010 | VanTassel et al. | |
| 7,735,493 | B2 | 6/2010 | van der Burg et al. | |
| 7,780,694 | B2 | 8/2010 | Palmer et al. | |
| 7,794,472 | B2 | 9/2010 | Eidenschink et al. | |
| 7,799,049 | B2 | 9/2010 | Ostrovsky et al. | |
| 7,803,171 | B1 | 9/2010 | Uflacker | |
| 7,811,300 | B2 | 10/2010 | Feller, III et al. | |
| 7,811,314 | B2 | 10/2010 | Fierens et al. | |
| 7,862,500 | B2 | 1/2011 | Khairkhahan et al. | |
| 7,927,365 | B2 | 4/2011 | Fierens et al. | |
| 7,959,645 | B2 | 6/2011 | WasDyke et al. | |
| 7,972,359 | B2 | 7/2011 | Kreidler | |
| 8,025,495 | B2 | 9/2011 | Hardert et al. | |
| 8,043,329 | B2 | 10/2011 | Khairkhahan et al. | |
| 8,052,715 | B2 | 11/2011 | Quinn et al. | |
| 8,062,282 | B2 | 11/2011 | Kolb | |
| 8,080,032 | B2 | 12/2011 | van der Burg et al. | |
| 8,097,015 | B2 | 1/2012 | Devellian | |
| 8,221,384 | B2 | 7/2012 | Frazier et al. | |
| 8,221,445 | B2 | 7/2012 | van Tassel et al. | |
| 8,246,648 | B2 | 8/2012 | Tekulve | |
| 8,287,563 | B2 | 10/2012 | Khairkhahan et al. | |
| 8,323,309 | B2 | 12/2012 | Khairkhahan et al. | |
| 8,388,672 | B2 | 3/2013 | Khairkhahan et al. | |
| 8,491,623 | B2 | 7/2013 | Vogel et al. | |
| 8,523,897 | B2 | 9/2013 | van der Burg et al. | |
| 8,535,343 | B2 | 9/2013 | van der Burg et al. | |
| 8,562,509 | B2 | 10/2013 | Bates | |
| 8,663,273 | B2 | 3/2014 | Khairkhahan et al. | |
| 8,685,055 | B2 | 4/2014 | VanTassel et al. | |
| 8,740,931 | B2 | 6/2014 | Snow | |
| 8,834,519 | B2 | 9/2014 | van der Burg et al. | |
| 8,845,711 | B2 | 9/2014 | Miles et al. | |
| 8,998,944 | B2 | 4/2015 | Thornton | |
| 9,034,006 | B2 | 5/2015 | Quinn et al. | |
| 9,132,000 | B2 | 9/2015 | VanTassel et al. | |
| 9,168,043 | B2 | 10/2015 | van der Burg et al. | |
| 9,186,152 | B2 | 11/2015 | Campbell et al. | |
| 9,211,124 | B2 | 12/2015 | Campbell et al. | |
| 9,445,895 | B2 | 9/2016 | Kreidler | |
| 9,554,806 | B2 | 1/2017 | Larsen et al. | |
| 9,561,037 | B2 | 2/2017 | Fogarty et al. | |
| 9,561,097 | B1 | 2/2017 | Kim et al. | |
| 9,629,636 | B2 | 4/2017 | Fogarty et al. | |
| 9,700,323 | B2 | 7/2017 | Clark | |
| 9,730,701 | B2 | 8/2017 | Tischler et al. | |
| 9,883,936 | B2 | 2/2018 | Sutton et al. | |
| 9,913,652 | B2 | 3/2018 | Bridgeman et al. | |
| 9,943,299 | B2 | 4/2018 | Khairkhahan et al. | |
| 9,943,315 | B2 | 4/2018 | Kaplan et al. | |
| 10,071,181 | B1 | 9/2018 | Penegor et al. | |
| 10,076,335 | B2 | 9/2018 | Zaver et al. | |
| 10,111,645 | B2 | 10/2018 | Fearnot et al. | |
| 10,143,458 | B2 | 12/2018 | Kreidler | |
| 10,258,454 | B2 | 4/2019 | Molgaard-Nielsen et al. | |
| 10,603,020 | B2 | 3/2020 | Rudman et al. | |
| 10,939,986 | B2 | 3/2021 | Chen et al. | |
| 11,039,822 | B2 | 6/2021 | Wang et al. | |
| 2001/0000797 | A1 | 5/2001 | Mazzocchi | |
| 2001/0020181 | A1 | 9/2001 | Layne | |
| 2001/0034537 | A1 | 10/2001 | Shaw et al. | |
| 2001/0037141 | A1 | 11/2001 | Yee et al. | |
| 2002/0022860 | A1 | 2/2002 | Borillo et al. | |
| 2002/0035374 | A1 | 3/2002 | Borillo et al. | |
| 2002/0045931 | A1 | 4/2002 | Sogard et al. | |
| 2002/0062133 | A1 | 5/2002 | Gilson et al. | |
| 2002/0082638 | A1 | 6/2002 | Porter et al. | |
| 2002/0082675 | A1 | 6/2002 | Myers | |
| 2002/0099439 | A1 | 7/2002 | Schwartz et al. | |
| 2002/0111647 | A1 | 8/2002 | Khairkhahan et al. | |
| 2002/0138094 | A1 | 9/2002 | Borillo et al. | |
| 2002/0138097 | A1 | 9/2002 | Ostrovsky et al. | |
| 2002/0169475 | A1 | 11/2002 | Gainor et al. | |
| 2002/0177855 | A1 | 11/2002 | Greene, Jr. et al. | |
| 2003/0017775 | A1 | 1/2003 | Dong et al. | |
| 2003/0023262 | A1 | 1/2003 | Welch | |
| 2003/0023266 | A1 | 1/2003 | Borillo et al. | |
| 2003/0057156 | A1 | 3/2003 | Peterson et al. | |
| 2003/0060871 | A1 | 3/2003 | Hill et al. | |
| 2003/0120337 | A1 | 6/2003 | Van Tassel et al. | |
| 2003/0181942 | A1 | 9/2003 | Sutton et al. | |
| 2003/0191517 | A1* | 10/2003 | Osborne .................. | A61F 2/07<br>623/1.13 |
| 2003/0191526 | A1 | 10/2003 | Van Tassel et al. | |
| 2003/0195555 | A1 | 10/2003 | Khairkhahan et al. | |
| 2003/0204203 | A1 | 10/2003 | Khairkhahan et al. | |
| 2003/0208214 | A1 | 11/2003 | Loshakove et al. | |
| 2003/0220667 | A1 | 11/2003 | van der Burg et al. | |
| 2004/0034366 | A1 | 2/2004 | van der Burg et al. | |
| 2004/0049210 | A1 | 3/2004 | VanTassel et al. | |
| 2004/0093012 | A1 | 5/2004 | Cully et al. | |
| 2004/0098031 | A1 | 5/2004 | van der Burg et al. | |
| 2004/0117004 | A1 | 6/2004 | Osborne et al. | |
| 2004/0122467 | A1 | 6/2004 | VanTassel et al. | |
| 2004/0127935 | A1 | 7/2004 | VanTassel et al. | |
| 2004/0158274 | A1 | 8/2004 | WasDyke | |

(56) References Cited

U.S. PATENT DOCUMENTS

| | | | |
|---|---|---|---|
| 2004/0186486 | A1 | 9/2004 | Roue et al. |
| 2004/0215230 | A1 | 10/2004 | Frazier et al. |
| 2004/0220610 | A1 | 11/2004 | Kreidler et al. |
| 2004/0220682 | A1 | 11/2004 | Evine et al. |
| 2004/0230222 | A1 | 11/2004 | van der Burg et al. |
| 2005/0004652 | A1 | 1/2005 | van der Burg et al. |
| 2005/0015109 | A1 | 1/2005 | Lichtenstein |
| 2005/0038470 | A1 | 2/2005 | van der Burg et al. |
| 2005/0049573 | A1 | 3/2005 | Van Tassel et al. |
| 2005/0070952 | A1 | 3/2005 | Devellian |
| 2005/0113861 | A1 | 5/2005 | Corcoran et al. |
| 2005/0125020 | A1 | 6/2005 | Meade et al. |
| 2005/0177182 | A1 | 8/2005 | van der Burg et al. |
| 2005/0203568 | A1 | 9/2005 | Burg et al. |
| 2005/0283186 | A1 | 12/2005 | Berrada et al. |
| 2005/0288704 | A1 | 12/2005 | Cartier et al. |
| 2006/0015136 | A1 | 1/2006 | Besselink |
| 2006/0030877 | A1 | 2/2006 | Martinez et al. |
| 2006/0052816 | A1 | 3/2006 | Bates et al. |
| 2006/0100658 | A1 | 5/2006 | Obana et al. |
| 2006/0155323 | A1 | 7/2006 | Porter et al. |
| 2007/0066993 | A1 | 3/2007 | Kreidler |
| 2007/0083227 | A1 | 4/2007 | van der Burg et al. |
| 2007/0083230 | A1 | 4/2007 | Javois |
| 2007/0150041 | A1 | 6/2007 | Evans et al. |
| 2007/0156123 | A1 | 7/2007 | Moll et al. |
| 2007/0162048 | A1 | 7/2007 | Quinn et al. |
| 2007/0185471 | A1 | 8/2007 | Johnson |
| 2008/0275536 | A1 | 11/2008 | Zarins et al. |
| 2009/0005803 | A1 | 1/2009 | Batiste |
| 2009/0062841 | A1 | 3/2009 | Amplatz et al. |
| 2009/0099647 | A1 | 4/2009 | Glimsdale et al. |
| 2009/0105747 | A1 | 4/2009 | Chanduszko et al. |
| 2009/0112249 | A1 | 4/2009 | Miles et al. |
| 2009/0171386 | A1 | 7/2009 | Amplatz et al. |
| 2009/0254195 | A1 | 10/2009 | Khairkhan et al. |
| 2009/0318948 | A1 | 12/2009 | Linder et al. |
| 2010/0004726 | A1 | 1/2010 | Hancock et al. |
| 2010/0016953 | A1 | 1/2010 | Sisken et al. |
| 2010/0049238 | A1 | 2/2010 | Simpson |
| 2010/0106178 | A1 | 4/2010 | Obermiller et al. |
| 2010/0256669 | A1 | 10/2010 | Harris et al. |
| 2010/0324585 | A1 | 12/2010 | Miles et al. |
| 2011/0054515 | A1 | 3/2011 | Bridgeman et al. |
| 2011/0082495 | A1 | 4/2011 | Ruiz |
| 2011/0098525 | A1 | 4/2011 | Kermode et al. |
| 2011/0218566 | A1 | 9/2011 | van der Burg et al. |
| 2011/0301630 | A1 | 12/2011 | Hendriksen et al. |
| 2012/0029553 | A1 | 2/2012 | Quinn et al. |
| 2012/0035643 | A1 | 2/2012 | Khairkhahan et al. |
| 2012/0065662 | A1 | 3/2012 | van der Burg et al. |
| 2012/0125619 | A1 | 5/2012 | Wood et al. |
| 2012/0172654 | A1 | 7/2012 | Bates |
| 2012/0172927 | A1 | 7/2012 | Campbell et al. |
| 2012/0239077 | A1 | 9/2012 | Zaver et al. |
| 2012/0239083 | A1 | 9/2012 | Kreidler |
| 2012/0245619 | A1 | 9/2012 | Guest |
| 2012/0283585 | A1 | 11/2012 | Werneth et al. |
| 2012/0283773 | A1 | 11/2012 | Van Tassel et al. |
| 2012/0323267 | A1 | 12/2012 | Ren |
| 2013/0006343 | A1 | 1/2013 | Kassab et al. |
| 2013/0012982 | A1 | 1/2013 | Khairkhahan et al. |
| 2013/0018413 | A1 | 1/2013 | Oral et al. |
| 2013/0110154 | A1 | 5/2013 | van der Burg et al. |
| 2013/0131717 | A1 | 5/2013 | Glimsdale |
| 2013/0165735 | A1 | 6/2013 | Khairkhahan et al. |
| 2013/0178889 | A1 | 7/2013 | Miles et al. |
| 2013/0211492 | A1 | 8/2013 | Schneider et al. |
| 2013/0331884 | A1 | 12/2013 | Van der Burg et al. |
| 2014/0005714 | A1 | 1/2014 | Quick et al. |
| 2014/0018841 | A1 | 1/2014 | Peiffer et al. |
| 2014/0039536 | A1 | 2/2014 | Cully et al. |
| 2014/0046360 | A1 | 2/2014 | van der Burg et al. |
| 2014/0081314 | A1 | 3/2014 | Zaver et al. |
| 2014/0100596 | A1 | 4/2014 | Rudman et al. |
| 2014/0142612 | A1 | 5/2014 | Li et al. |
| 2014/0148842 | A1 | 5/2014 | Khairkhahan et al. |
| 2014/0163605 | A1 | 6/2014 | VanTassel et al. |
| 2014/0188157 | A1 | 7/2014 | Clark |
| 2014/0303719 | A1 | 10/2014 | Cox et al. |
| 2014/0336612 | A1 | 11/2014 | Frydlewski et al. |
| 2014/0336699 | A1 | 11/2014 | van der Burg et al. |
| 2015/0005810 | A1 | 1/2015 | Center et al. |
| 2015/0039021 | A1 | 2/2015 | Khairkhahan et al. |
| 2015/0080903 | A1 | 3/2015 | Dillard et al. |
| 2015/0196300 | A1 | 7/2015 | Tischler et al. |
| 2015/0230909 | A1 | 8/2015 | Zaver et al. |
| 2015/0238197 | A1 | 8/2015 | Quinn et al. |
| 2015/0305727 | A1 | 10/2015 | Karimov et al. |
| 2015/0313604 | A1 | 11/2015 | Roue et al. |
| 2015/0313605 | A1 | 11/2015 | Griffin |
| 2015/0327979 | A1 | 11/2015 | Quinn et al. |
| 2015/0374491 | A1 | 12/2015 | Kreidler |
| 2016/0051358 | A1 | 2/2016 | Sutton et al. |
| 2016/0058539 | A1 | 3/2016 | VanTassel et al. |
| 2016/0066922 | A1 | 3/2016 | Bridgeman et al. |
| 2016/0106437 | A1 | 4/2016 | van der Burg et al. |
| 2016/0192942 | A1 | 7/2016 | Strauss et al. |
| 2016/0287259 | A1 | 10/2016 | Hanson et al. |
| 2016/0331382 | A1 | 11/2016 | Center et al. |
| 2016/0374657 | A1 | 12/2016 | Kreidler |
| 2017/0027552 | A1 | 2/2017 | Turkington et al. |
| 2017/0042550 | A1 | 2/2017 | Chakraborty et al. |
| 2017/0056166 | A1 | 3/2017 | Ratz et al. |
| 2017/0100112 | A1 | 4/2017 | van der Burg et al. |
| 2017/0119400 | A1 | 5/2017 | Amplatz et al. |
| 2017/0181751 | A1 | 6/2017 | Larsen et al. |
| 2017/0340336 | A1 | 11/2017 | Osypka |
| 2018/0064446 | A1 | 3/2018 | Figulla et al. |
| 2018/0070950 | A1 | 3/2018 | Zaver et al. |
| 2018/0140412 | A1 | 5/2018 | Sutton et al. |
| 2018/0140413 | A1 | 5/2018 | Quinn et al. |
| 2018/0250014 | A1 | 9/2018 | Melanson et al. |
| 2018/0310925 | A1 | 11/2018 | Inouye et al. |
| 2019/0046213 | A1 | 2/2019 | Gong et al. |
| 2019/0083224 | A1 | 3/2019 | Tessmer |
| 2019/0117367 | A1 | 4/2019 | Simpson |
| 2019/0125362 | A1 | 5/2019 | Tischler |
| 2019/0167242 | A1 | 6/2019 | Rowe et al. |
| 2019/0223883 | A1 | 7/2019 | Anderson et al. |
| 2019/0298380 | A1 | 10/2019 | Inouye et al. |
| 2019/0299011 | A1 | 10/2019 | Chu |
| 2020/0008812 | A1 | 1/2020 | Inouye et al. |
| 2020/0060801 | A1 | 2/2020 | Yang |
| 2020/0060849 | A1 | 2/2020 | Inouye et al. |
| 2020/0178981 | A1 | 6/2020 | Anderson et al. |
| 2021/0015596 | A1 | 1/2021 | Nigon |
| 2021/0059685 | A1 | 3/2021 | Groff et al. |

FOREIGN PATENT DOCUMENTS

| | | | |
|---|---|---|---|
| CN | 106859722 | A | 6/2017 |
| DE | 10201004476 | A1 | 3/2012 |
| EP | 1523957 | A2 | 4/2005 |
| EP | 1595504 | A1 | 11/2005 |
| EP | 2074953 | A1 | 1/2009 |
| EP | 2481381 | A1 | 8/2012 |
| EP | 2928420 | A1 | 10/2015 |
| EP | 3072461 | A1 | 9/2016 |
| EP | 3372173 | A2 | 9/2018 |
| JP | 2003532457 | A | 11/2003 |
| JP | 2005324019 | A | 11/2005 |
| JP | 2007513684 | A | 5/2007 |
| JP | 2009160402 | A | 7/2009 |
| JP | 2012501793 | A | 1/2012 |
| WO | 9313712 | A1 | 7/1993 |
| WO | 9504132 | A1 | 2/1995 |
| WO | 9522359 | A1 | 8/1995 |
| WO | 9601591 | A1 | 1/1996 |
| WO | 9640356 | A1 | 12/1996 |
| WO | 9721402 | A1 | 6/1997 |
| WO | 9726939 | A1 | 7/1997 |
| WO | 9728749 | A1 | 8/1997 |
| WO | 9735522 | A1 | 10/1997 |

(56) References Cited

FOREIGN PATENT DOCUMENTS

| | | | |
|---|---|---|---|
| WO | 9802100 A1 | 1/1998 | |
| WO | 9817187 A1 | 4/1998 | |
| WO | 9822026 A1 | 5/1998 | |
| WO | 9823322 A1 | 6/1998 | |
| WO | 9827868 A1 | 7/1998 | |
| WO | 9905977 A1 | 2/1999 | |
| WO | 9907289 A1 | 2/1999 | |
| WO | 9908607 A1 | 2/1999 | |
| WO | 9923976 A1 | 5/1999 | |
| WO | 9925252 A1 | 5/1999 | |
| WO | 9930640 A1 | 6/1999 | |
| WO | 9944510 A1 | 9/1999 | |
| WO | 9959479 A1 | 11/1999 | |
| WO | 0001308 A1 | 1/2000 | |
| WO | 0016705 A1 | 3/2000 | |
| WO | 0027292 A1 | 5/2000 | |
| WO | 0035352 A1 | 6/2000 | |
| WO | 0053120 A1 | 9/2000 | |
| WO | 0067669 A1 | 11/2000 | |
| WO | 0108743 A1 | 2/2001 | |
| WO | 0115629 A1 | 3/2001 | |
| WO | 0121247 A1 | 3/2001 | |
| WO | 0126726 A1 | 4/2001 | |
| WO | 0130266 A1 | 5/2001 | |
| WO | 0130267 A1 | 5/2001 | |
| WO | 0130268 A1 | 5/2001 | |
| WO | 0170119 A1 | 9/2001 | |
| WO | 0215793 A2 | 2/2002 | |
| WO | 0224106 A2 | 3/2002 | |
| WO | 02071977 A2 | 9/2002 | |
| WO | 03007825 A1 | 1/2003 | |
| WO | 03008030 A2 | 1/2003 | |
| WO | 03032818 A1 | 4/2003 | |
| WO | 2004012629 A1 | 2/2004 | |
| WO | 2007044536 A1 | 4/2007 | |
| WO | 2010024801 A1 | 3/2010 | |
| WO | 2010081033 A1 | 7/2010 | |
| WO | 2013060855 A1 | 5/2013 | |
| WO | 2013159065 A1 | 10/2013 | |
| WO | 2014011865 A1 | 1/2014 | |
| WO | 2014018907 A1 | 1/2014 | |
| WO | 2014078698 A2 | 5/2014 | |
| WO | 2014089129 A1 | 6/2014 | |
| WO | 201406239 A1 | 7/2014 | |
| WO | 2015164836 A1 | 10/2015 | |
| WO | 2016087145 A1 | 6/2016 | |
| WO | 2018017935 A1 | 1/2018 | |
| WO | 2018187732 A1 | 10/2018 | |
| WO | 2019084358 A1 | 5/2019 | |
| WO | WO-2021052486 A1 * | 3/2021 | ....... A61B 17/12177 |

OTHER PUBLICATIONS

International Search Report and Written Opinion dated Aug. 3, 2004 for International Application No. PCT/US2004/008109.
International Search Report and Written Opinion dated Feb. 15, 2000 for International Application No. PCT/US99/26325.
International Search Report dated May 20, 2003 for International Application No. PCT/US02/33808.
Written Opinion dated Nov. 17, 2003 for International Application No. PCT/US/02/33808.
International Search Report and Written Opinion dated Aug. 21, 2018 for International Application No. PCT/US2018/029684.
Cragg et al., "A New Percutaneous Vena Cava Filter," American Journal of Radiology, Sep. 1983, pp. 601-604, vol. 141.
Cragg et al, "Nonsurgical Placement of Arterial Endoprostheses: A New Technique Using Nitinol Wire," Radiology, Apr. 1983, pp. 261-263, vol. 147, No. 1.
Lock et al., "Transcatheter Closure of Atrial Septal Defects." Circulation, May 1989, pp. 1091-1099, vol. 79, No. 5.
Lock et al., "Transcatheter Umbrella Closure of Congenital Heart Defects," Circulation, Mar. 1987, pp. 593-599, vol. 75, No. 3.
Rashkind et al., "Nonsurgical closure of patent ductus arteriosus: clinical application of the Rashkind PDA Occluder System," Circulation, Mar. 1987, pp. 583-592, vol. 75, No. 3.
Rosengart et al., "Percutaneous and Minimally Invasive Valve Procedures," Circulation, Apr. 1, 2008, pp. 1750-1767, vol. 117.
Ruttenberg, "Nonsurgical Therapy of Cardiac Disorders," Pediatric Consult, 1986, Pages not numbered, vol. 5, No. 2.
Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.
Wessel et al., "Outpatient Closure of the Patent Ductus Arteriousus," Circulation, 1988, pp. 1068-1071, vol. 77, No. 5.
Tung et al., U.S. Appl. No. 61/559,941, filed Nov. 15, 2011.
Yue Yu et al., U.S. Appl. No. 61/557,880, filed Dec. 20, 2011.
Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.
International Search Report and Written Opinion dated Apr. 22, 2014 for International Application No. PCT/US2013/078454.
Aryana et al., "Incomplete Closure of the Left Atrial Appendage: Implication and Management." Curr Cardiol Rep., 18(9):82, 2016.
Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.
University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.
Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.
Romero et al., "Left Atrial Appendage Closure Devices," Clinical Medicine Insights: Cardiology, vol. 8, pp. 45-52, 2014.
Invitation To Pay Additional Fees And, Where Applicable, Protest Fee, mailed Oct. 13, 2016.
International Search Report and Written Opinion dated Oct. 14, 2019 for International Application No. PCT/US2019/047452.
International Search Report and Written Opinion dated Oct. 27, 2017 for International Application No. PCT/US2017/048150.
International Search Report and Written Opinion dated Jan. 21, 2019 for International Application No. PCT/US2018/051953.
International Search Report and Written Opinion dated Oct. 13, 2016 for International Application No. PCT/US2016/043363.
International Search Report and Written Opinion dated Mar. 17, 2020, for International Application No. PCT/US2019/065243.
International Search Report and Written Opinion dated Sep. 9, 2019 for International Application No. PCT/US2019/033698.
Blackshear et al; "Appendage Obliteration to Reduce Stroke in Cardiac Surgical Patients with Atrial Fibrillation", Ann. Thoracic Surgery, pp. 755-759, 1996.
Lindsay, "Obliteration of the Left Atrial Appendage: A Concept Worth Testing", Ann. Thoracic Surgery, 1996.
Invitation To Pay Additional Fees dated Feb. 22, 2019 for International Application No. PCT/US2018/066163.
International Search Report and Written Opinion dated Oct. 23, 2020 for International Application No. PCT/US2020/042192.
International Search Report and Written Opinion dated Dec. 6, 2022 for International Application No. PCT/US2022/042696.
LabCE. https://www.labce.com/spg579126_red_blood_cell_rbc_size_variation.aspx. "Red Blood Cell (RBC) Size Variation", 2019.

* cited by examiner

TWISTED TIP SOFT TISSUE ANCHORS

CROSS-REFERENCE TO RELATED APPLICATIONS

This application claims the benefit of priority of U.S. Provisional Application No. 63/277,406 filed Nov. 9, 2021, the entire disclosure of which is hereby incorporated by reference.

TECHNICAL FIELD

The disclosure relates generally to medical devices and more particularly to occlusive implants adapted for use in percutaneous medical procedures including implantation into the left atrial appendage (LAA) of a heart.

BACKGROUND

The left atrial appendage is a small organ attached to the left atrium of the heart. During normal heart function, as the left atrium constricts and forces blood into the left ventricle, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage.

Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation originate in the left atrial appendage. As a treatment, medical devices have been developed which are deployed to close off the left atrial appendage. Of the known medical devices and methods, each has certain advantages and disadvantages. Soft tissue anchors for medical devices often are formed from wire barbs that have little flexibility in design. Barb height and angle are usually the main design parameters. These types of anchors may not fully retain and/or anchor the medical device or implant in all clinical situations, possibly leading to device embolization, shifting, etc. There is an ongoing need to provide alternative medical devices and methods for manufacturing and using medical devices.

SUMMARY

In one example, an occlusive implant may comprise an expandable framework having a central longitudinal axis extending from a proximal end to a distal end, the expandable framework being configured to shift between a collapsed configuration and an expanded configuration. The expandable framework includes a plurality of anchor members extending radially outward from the expandable framework in the expanded configuration, each anchor member including at least one base portion fixedly secured to the expandable framework and a plurality of anchor tips extending from each base portion. Each base portion extends longitudinally along the expandable framework.

In addition or alternatively to any example described herein, each of the plurality of anchor members includes at least two twisted filaments.

In addition or alternatively to any example described herein, each of the at least two twisted filaments forms one of the plurality of anchor tips.

In addition or alternatively to any example described herein, each of the plurality of anchor members includes at least three twisted filaments.

In addition or alternatively to any example described herein, each of the at least three twisted filaments forms one of the plurality of anchor tips.

In addition or alternatively to any example described herein, each anchor tip of the plurality of anchor tips is configured to penetrate tissue.

In addition or alternatively to any example described herein, the plurality of anchor tips extending from each base portion collectively form a tissue shelf configured to limit penetration of the plurality of anchor tips into tissue.

In addition or alternatively to any example described herein, each anchor member includes a pedestal portion disposed between each base portion and the plurality of anchor tips extending from each base portion such that the pedestal portion extends outward from the base portion and the plurality of anchor tips extends outward from the pedestal portion.

In addition or alternatively to any example described herein, each anchor member includes a bridge portion connecting two base portions fixedly secured to the expandable framework and a plurality of anchor tips extending from each base portion.

In addition or alternatively to any example described herein, a method of making an occlusive implant may comprise forming an expandable framework having a central longitudinal axis extending from a proximal end to a distal end, the expandable framework being configured to shift between a collapsed configuration and an expanded configuration; forming a plurality of anchor members, wherein each anchor member includes at least one base portion and a plurality of anchor tips extending from each base portion; and fixedly attaching each base portion to the expandable framework. Each anchor member extends radially outward from the expandable framework in the expanded configuration. Each base portion extends longitudinally along the expandable framework.

In addition or alternatively to any example described herein, forming the plurality of anchor members includes twisting at least two filaments together to form each anchor member, each filament having a first end and a second end.

In addition or alternatively to any example described herein, forming the plurality of anchor members includes separating and/or splaying apart the first ends of the at least two filaments to form the plurality of anchor tips of a first base portion of the at least one base portion and separating and/or splaying apart the second ends of the at least two filaments to form the plurality of anchor tips of a second base portion of the at least one base portion, wherein portions of the at least two filaments that remain twisted together form each base portion and a bridge portion connecting each anchor member of the plurality of anchor members.

In addition or alternatively to any example described herein, each base portion is formed from twisting the first ends of the at least two filaments together and the second ends of the at least two filaments each form one of the plurality of anchor tips.

In addition or alternatively to any example described herein, forming the plurality of anchor members includes twisting at least three filaments together to form each anchor member, each filament having a first end and a second end.

In addition or alternatively to any example described herein, each base portion is formed from twisting the first ends of the at least three filaments together and the second ends of the at least three filaments each form one of the plurality of anchor tips.

In addition or alternatively to any example described herein, a method of making an occlusive implant may comprise forming an expandable framework having a central longitudinal axis extending from a proximal end to a distal end, the expandable framework being configured to shift between a collapsed configuration and an expanded configuration; twisting at least two first filaments together to form a first anchor member including at least one base portion and a plurality of first anchor tips extending from each base portion of the first anchor member; twisting at least two second filaments together to form a second anchor member including at least one base portion and a plurality of second anchor tips extending from each base portion of the second anchor member; fixedly attaching the first anchor member to the expandable framework such that each base portion of the first anchor member extends longitudinally along the expandable framework; and fixedly attaching the second anchor member to the expandable framework such that each base portion of the second anchor member extends longitudinally along the expandable framework.

In addition or alternatively to any example described herein, each of the at least two first filaments and each of the at least two second filaments are formed from a metallic material.

In addition or alternatively to any example described herein, the plurality of first anchor tips extending from each base portion of the first anchor member is spaced apart from each other in the expanded configuration.

In addition or alternatively to any example described herein, the plurality of second anchor tips extending from each base portion of the second anchor member is spaced apart from each other in the expanded configuration.

In addition or alternatively to any example described herein, the plurality of first anchor tips collectively forms a first tissue shelf configured to limit penetration of the plurality of first anchor tips into tissue. The plurality of second anchor tips collectively forms a second tissue shelf configured to limit penetration of the plurality of second anchor tips into tissue.

The above summary of some embodiments, aspects, and/or examples is not intended to describe each embodiment or every implementation of the present disclosure. The figures and the detailed description more particularly exemplify aspects of these embodiments.

BRIEF DESCRIPTION OF THE DRAWINGS

The disclosure may be more completely understood in consideration of the following detailed description in connection with the accompanying drawings, in which.

Figure 1:
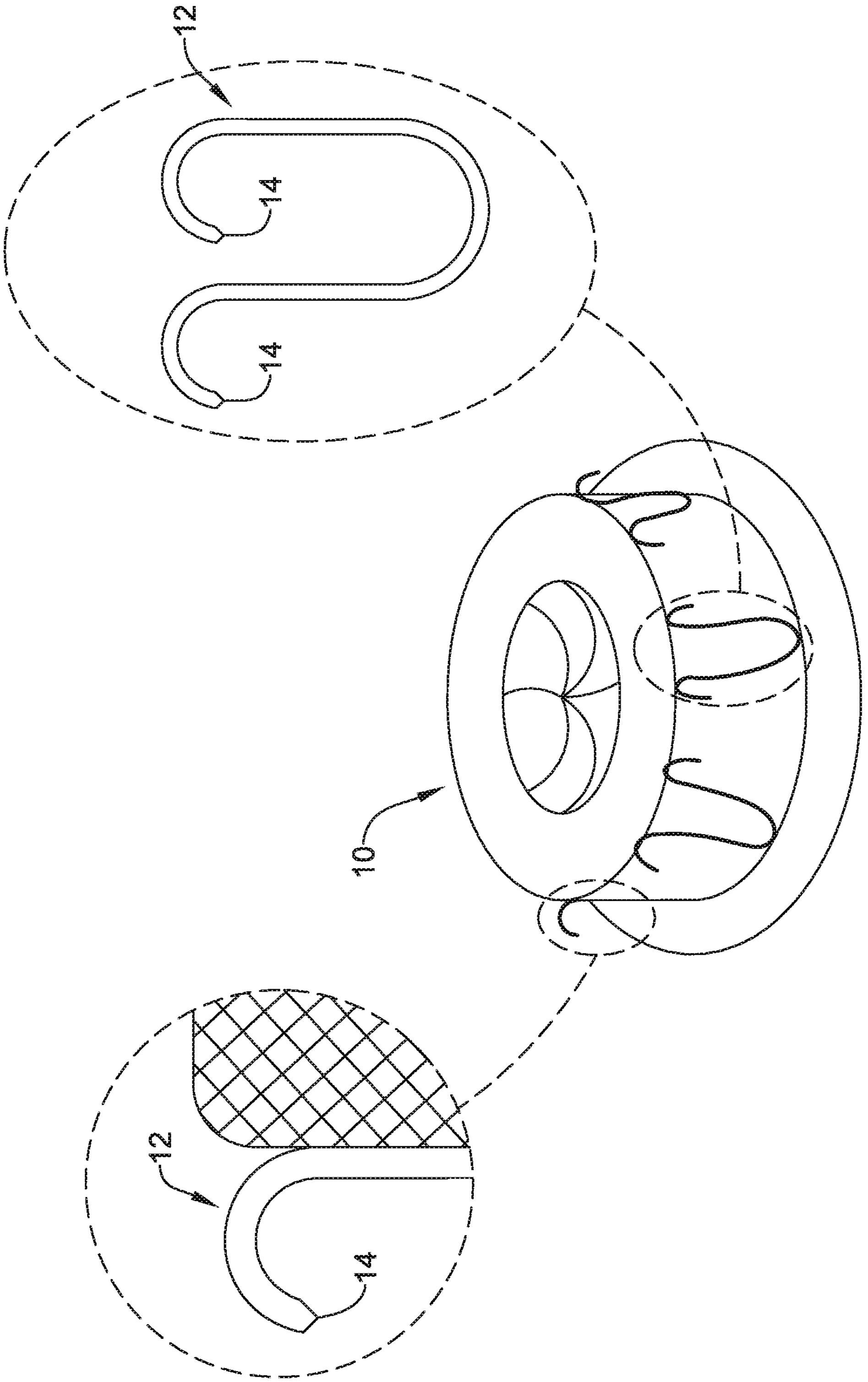
FIG. 1 Prior Art
FIGS. 1-2 schematically illustrate prior art medical devices having soft tissue anchors formed from a wire barb.

While aspects of the disclosure are amenable to various modifications and alternative forms, examples are shown in the drawings and described herein. It should be understood, however, that the intention is not to limit aspects of the disclosure to the particular embodiments described. On the contrary, the disclosure shall cover all modifications, equivalents, and alternatives falling within the spirit and scope thereof.

DETAILED DESCRIPTION

The following description should be read with reference to the drawings, which are not necessarily to scale, wherein like reference numerals indicate like elements throughout the several views. The detailed description and drawings are intended to illustrate but not limit the present disclosure. Those skilled in the art will recognize that the various elements described and/or shown may be arranged in various combinations and configurations without departing from the scope of the disclosure. The detailed description and drawings illustrate exemplary aspects of the disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, all elements of the present disclosure are not necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as “proximal”, “distal”, “advance”, “retract”, variants thereof, and the like, may be generally considered with respect to the positioning, direction, and/or operation of various elements relative to a user/operator/manipulator of the device, wherein “proximal” and “retract” indicate or refer to closer to or toward the user and “distal” and “advance” indicate or refer to farther from or away from the user. In some instances, the terms “proximal” and “distal” may be arbitrarily assigned in an effort to facilitate understanding of the disclosure, and such instances will be readily apparent to the skilled artisan. Other relative terms, such as “upstream”, “downstream”, “inflow”, and “outflow” refer to a direction of fluid flow within a lumen, such as a body lumen, a blood vessel, or within a device. Still other relative terms, such as “axial”, “circumferential”, “longitudinal”, “lateral”, “radial”, etc. and/or variants thereof generally refer to direction and/or orientation relative to a central longitudinal axis of the disclosed structure or device.

The term “extent” may be understood to mean the greatest measurement of a stated or identified dimension, unless the extent or dimension in question is preceded by or identified as a “minimum”, which may be understood to mean the smallest measurement of the stated or identified dimension. For example, “outer extent” may be understood to mean an outer dimension, “radial extent” may be understood to mean a radial dimension, “longitudinal extent” may be understood to mean a longitudinal dimension, etc. Each instance of an “extent” may be different (e.g., axial, longitudinal, lateral, radial, circumferential, etc.) and will be apparent to the skilled person from the context of the individual usage. Generally, an “extent” may be considered the greatest possible dimension measured according to the intended usage, while a “minimum extent” may be considered the smallest possible dimension measured according to the intended usage. In some instances, an “extent” may generally be measured orthogonally within a plane and/or cross-section, but may be, as will be apparent from the particular context, measured differently—such as, but not limited to, angularly, radially, circumferentially (e.g., along an arc), etc.

The terms “monolithic” and “unitary” shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to “an embodiment”, “some embodiments”, “other embodiments”, etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a “first” element may later be referred to as a “second” element, a “third” element, etc. or may be omitted entirely, and/or a different feature may be referred to as the “first” element. The meaning and/or designation in each instance will be apparent to the skilled practitioner.

The left atrial appendage may be attached to and in fluid communication with a left atrium of a patient’s heart. In some patients, the left atrial appendage may have a complex geometry and/or irregular surface area. Those of skill in the art will also recognize that the medical devices and methods disclosed herein may be adapted for various sizes and shapes of the left atrial appendage, as necessary. The left atrial appendage may include a generally longitudinal axis arranged along a depth of a main body of the left atrial appendage. The main body may include a wall and an ostium forming a proximal mouth. In some embodiments, a lateral extent of the ostium and/or the wall may be smaller or less than a depth of the main body along the longitudinal axis, or a depth of the main body may be greater than a lateral extent of the ostium and/or the wall. In some embodiments, the left atrial appendage may include a tail-like element associated with a distal portion of the main body, which element may protrude radially or laterally away from the main body.

Figure 2:
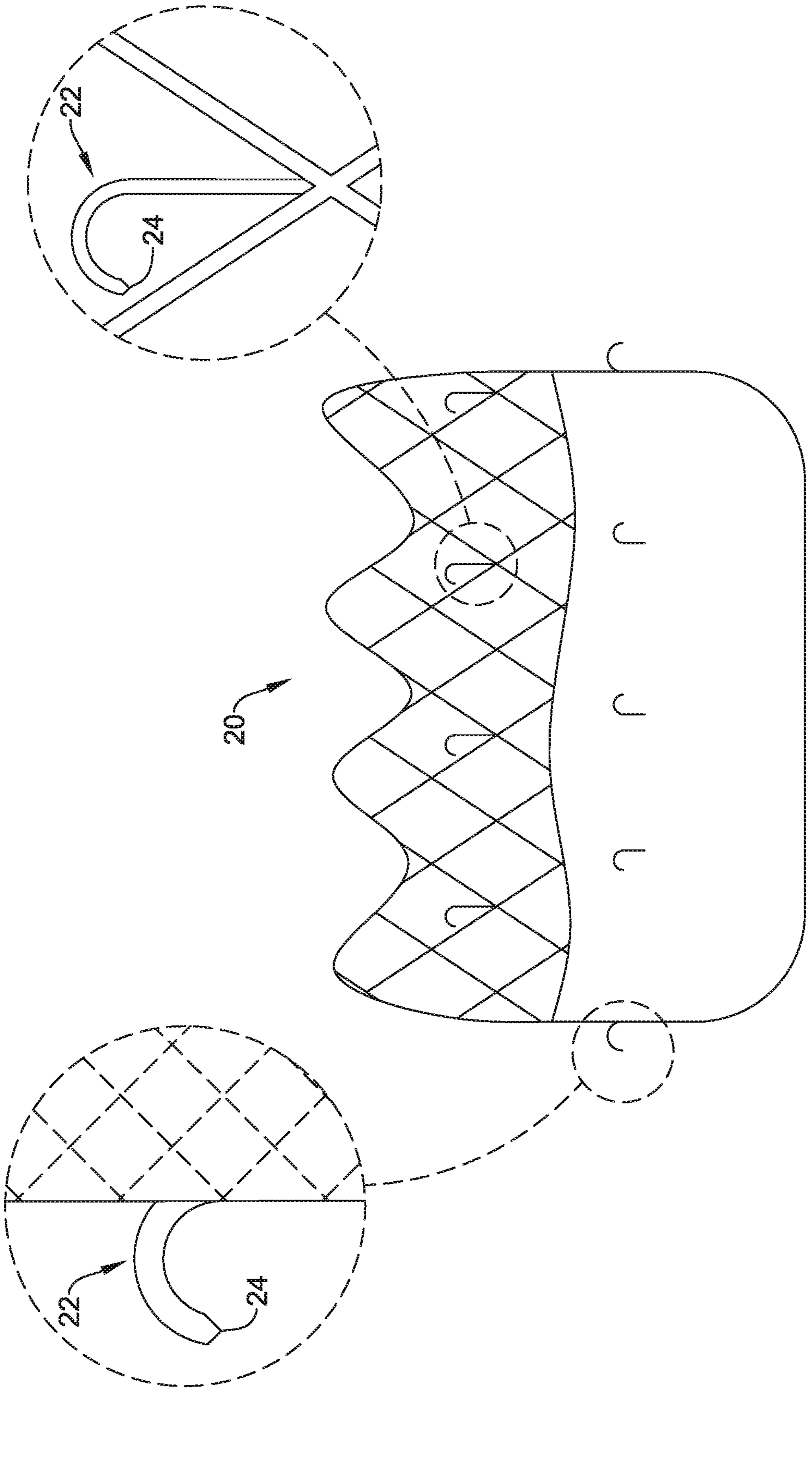
FIG. 2 Prior Art
Figure 3:
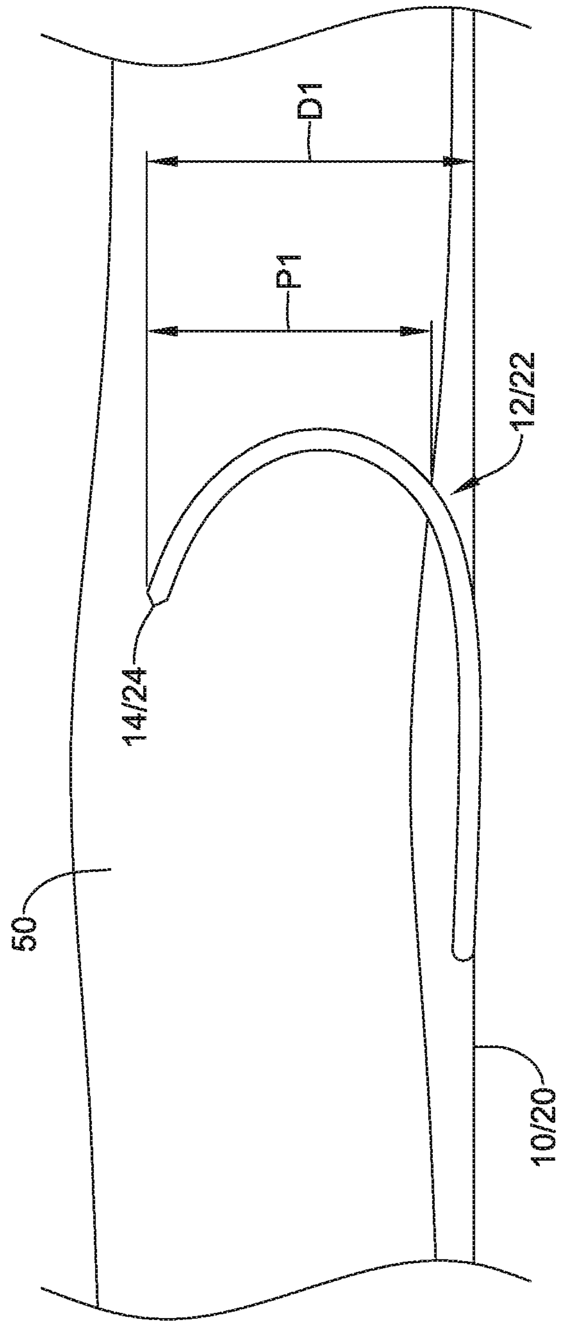
FIG. 3 Prior Art
FIGS. 3-3A illustrate penetration of the prior art soft tissue anchors into tissue.
Figure 3A:
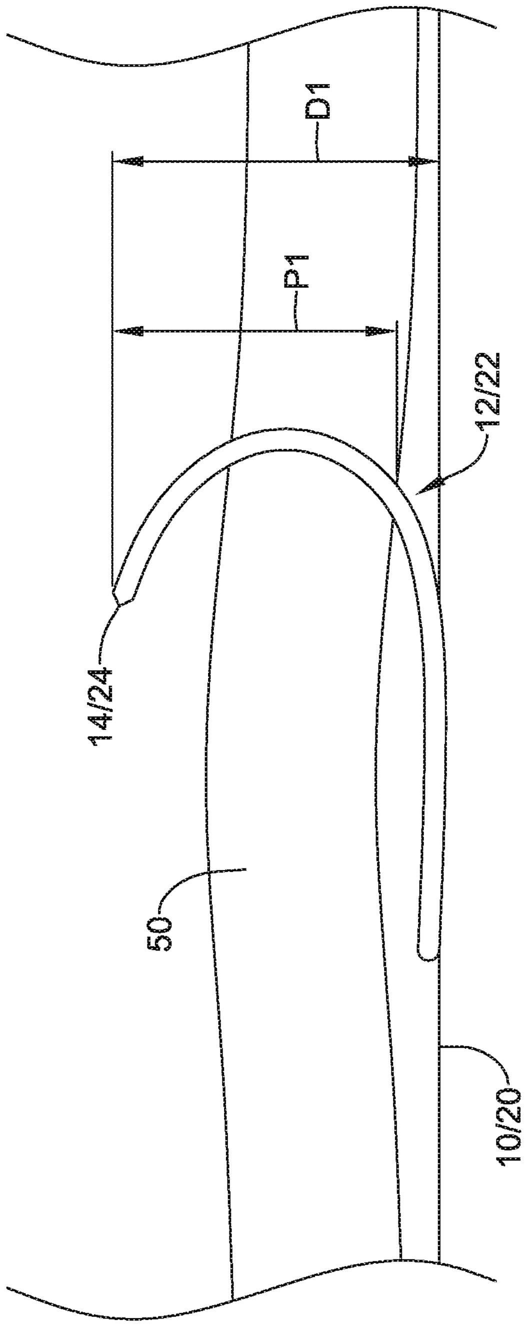
FIG. 3A Prior Art

FIG. 1 illustrates an occlusive implant 10 having a plurality of wire barbs 12 as anchoring elements. The plurality of wire barbs 12 have a single anchoring tip 14 at the ends of the plurality of wire barbs 12. FIG. 2 illustrates an occlusive implant 20 having a plurality of wire barbs 22 as anchoring elements. The plurality of wire barbs 22 have a single anchoring tip 24 at the ends of the plurality of wire barbs 22. Anchoring provided by the wire barbs may not be consistent in all clinical situations. FIG. 3 illustrates an example of the depth of penetration P1 of the plurality of wire barbs 12/22 into tissue 50 and the extension distance D1 of the outermost extent of the plurality of wire barbs 12/22 from the occlusive implant 10/20. In some situations, the thickness of the tissue 50 may vary. For example, the left atrial appendage may have varying tissue thickness about its circumference and/or length. As such, in some situations, the thickness of the tissue 50 may be insufficient for the depth of penetration of the plurality of wire barbs 12/22 to avoid completely passing through the tissue 50 and creating a puncture, as seen in FIG. 3A. Depth of penetration may be desirable for anchoring but may also be a detriment to repositioning and/or recapture of the occlusive implant. Additionally, completely penetrating the tissue 50 is undesirable for several reasons, including but not limited to leakage through the puncture and potential damage to adjacent tissues and/or body structures.

The following figures illustrate selected components and/or arrangements of an occlusive implant, an occlusive implant system, and/or methods of making and/or using the occlusive implant and/or the occlusive implant system. It should be noted that in any given figure, some features may not be shown, or may be shown schematically, for simplicity. Additional details regarding some of the components of the occlusive implant and/or the system may be illustrated in other figures in greater detail. While discussed in the context of occluding the left atrial appendage, the occlusive implant may also be used for other interventions and/or percutaneous medical procedures within a patient. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy. Additionally, while some elements may be shown and/or described in the singular, the figures and/or description shall apply to each instance of said element(s) present in the occlusive implant.

Figure 4:
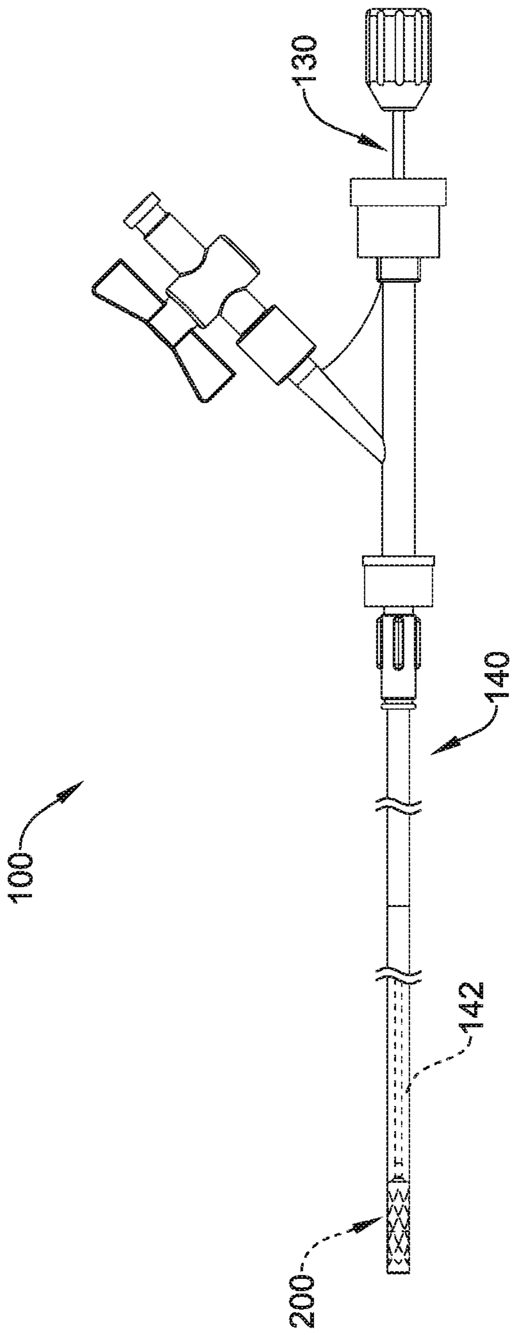
FIGS. 4-5 are side views of an occlusive implant system.
Figure 5:
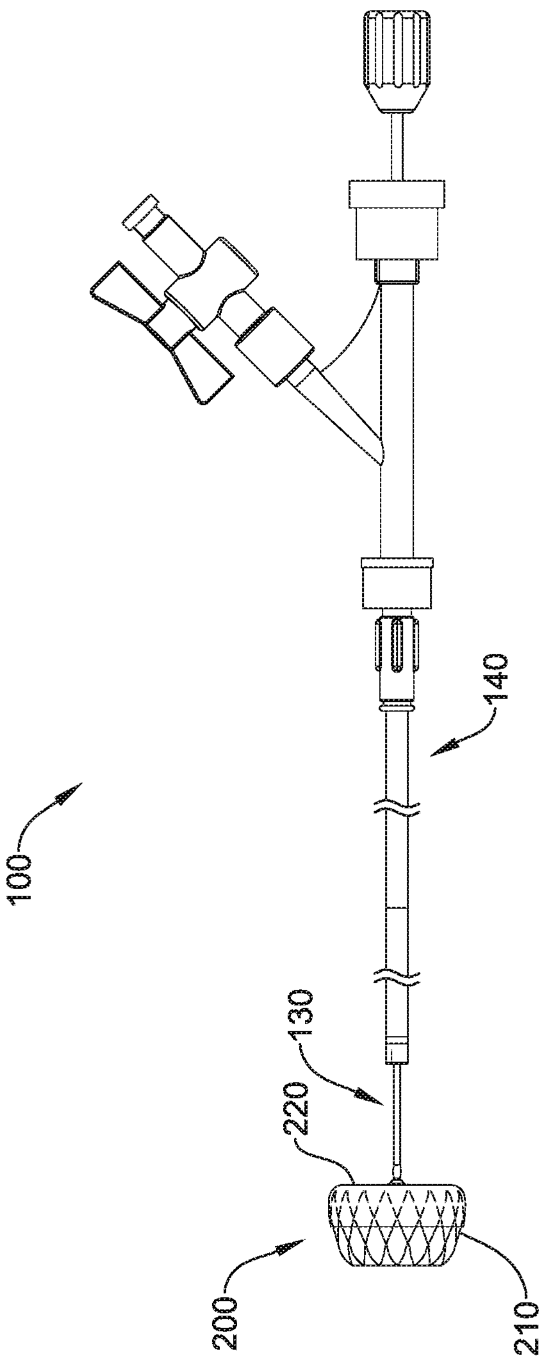

The figures illustrate selected components and/or arrangements of an occlusive implant system 100, shown schematically in FIGS. 4-5 for example. In some embodiments, the occlusive implant system 100 may include a delivery device that can be used for percutaneous delivery of an occlusive implant to an area of interest in the anatomy, such as a left atrial appendage. This, however, is not intended to be limiting as the occlusive implant system 100 and/or the delivery device may also be used for other interventions.

The occlusive implant system 100 may include a sheath 140 having a lumen 142 extending from a proximal opening to a distal opening, a core wire 130 slidably disposed within the lumen 142, and an occlusive implant 200 having an expandable framework 210 configure to shift between a collapsed configuration (e.g., FIG. 4), wherein the occlusive implant 200 is disposed within an implant containment area of the sheath 140 proximate a distal end of the sheath 140 and/or the distal opening in the collapsed configuration, and an expanded configuration (e.g., FIG. 5), wherein the occlusive implant 200 and/or the expandable framework 210 is configured to shift between the collapsed configuration and the expanded configuration when the occlusive implant 200 is disposed distal of the distal end of the sheath 140 and/or the distal opening, and/or when the occlusive implant 200 is distal of and/or outside of the implant containment area of the sheath 140. The occlusive implant 200 may be disposed at and/or releasably connected to a distal portion of the core wire 130. The core wire 130 may be slidably and/or rotatably disposed within the lumen 142 of the sheath 140 and/or the implant containment area of the sheath 140. In some embodiments, a proximal end of the core wire 130 may extend proximally of a proximal end of the sheath 140 and/or the proximal opening of the lumen 142 for manual manipulation by a clinician or practitioner. In some embodiments, the occlusive implant 200 may be removably attached, joined, or otherwise connected to the distal end of the core wire 130. The core wire 130 may be configured to and/or may be capable of axially translating the occlusive implant 200 relative to the sheath 140 and/or the implant containment area of the sheath 140. In one example, the core wire 130 may be advanced distally while the sheath 140 is held in a constant position. In another example, the core wire 130 may be advanced distally while the sheath 140 is retracted proximally. In yet another example, the core wire 130 may be held in a constant position while the sheath 140 is retracted proximally relative to the core wire 130 and/or the occlusive implant 200. Other configurations are also contemplated. The sheath 140 and/or the core wire 130 may have a selected level of axial stiffness and/or pushability characteristics while also having a selected level of flexibility to permit navigation through the patient's vasculature. Some suitable, but non-limiting, examples of materials for the occlusive implant system 100, the core wire 130, the sheath 140, and/or the occlusive implant 200, etc. are discussed below.

Figure 6:
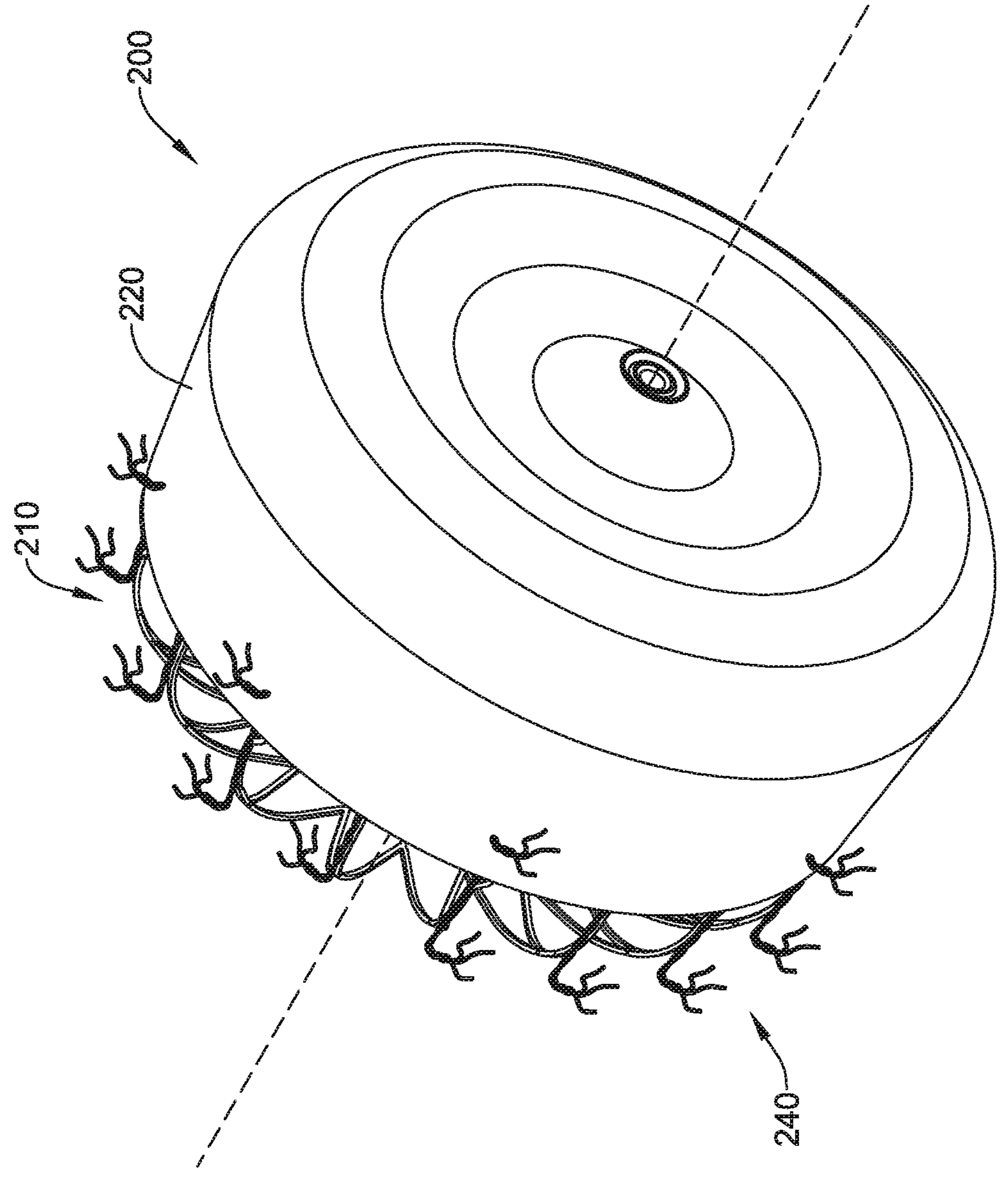
FIG. 6 illustrates selected aspects of an occlusive implant.

FIG. 6 illustrates selected aspects of an occlusive implant 200. In some embodiments, the occlusive implant 200 comprising the expandable framework 210 may be configured to shift axially and/or radially along a central longitudinal axis between the collapsed configuration and the expanded configuration. The expandable framework 210 may comprise a plurality of interconnected struts defining a plurality of cells. In some embodiments, the plurality of cells may be a plurality of closed cells. In some embodiments, the plurality of cells may be a plurality of open cells. In some embodiments, the plurality of cells may include a plurality of open cells and a plurality of closed cells in various combinations and/or arrangements. The expandable framework 210 may be compliant and substantially conform to and/or be in sealing engagement with the shape and/or geometry of an ostium and/or a lateral wall of a left atrial appendage in the expanded configuration. In some embodiments, the occlusive implant 200 may expand to a size, extent, or shape less than or different from a maximum unconstrained extent, as determined by the surrounding tissue, the ostium, and/or the lateral wall of the left atrial appendage. In some embodiments, reducing a thickness of various elements of the expandable framework 210 may increase the flexibility and compliance of the expandable framework 210 and/or the occlusive implant 200, thereby permitting the expandable framework 210 and/or the occlusive implant 200 to conform to the tissue around it, rather than forcing the tissue to conform to the expandable framework 210 and/or the occlusive implant 200.

The expandable framework 210 may include a proximal end and a distal end. In some embodiments, the expandable framework 210 may include a proximal hub configured to releasably attach, join, couple, engage, or otherwise connect to a distal end of the core wire 130. In some embodiments, the proximal hub of the expandable framework 210 may include a threaded insert coupled thereto. In some embodiments, the threaded insert may be configured to and/or adapted to couple with, join to, mate with, or otherwise engage a threaded member disposed at the distal end of the core wire 130. Other means of releasably coupling and/or engaging the proximal hub of the expandable framework 210 to the distal end of the core wire 130 are also contemplated. As noted herein, some features are not shown in every figure to improve clarity.

In some embodiments, the expandable framework 210 and/or the plurality of interconnected struts may be formed and/or cut from a tubular member. In some embodiments, the expandable framework 210 and/or the plurality of interconnected struts may be integrally formed and/or cut from a flat member or sheet, and then rolled or formed into a tubular structure and subsequently formed and/or heat set to the desired shape in the expanded configuration. Some exemplary means and/or methods of making and/or forming the expandable framework 210 and/or the plurality of interconnected struts include laser cutting, machining, punching, stamping, electro discharge machining (EDM), chemical dissolution, etc. Other means and/or methods are also contemplated. Alternatively, in some embodiments, the expandable framework 210 and/or the plurality of interconnected struts may be braided, woven, and/or otherwise intertwined from and/or using one or more individual filaments. Other configurations are also contemplated.

In some embodiments, the occlusive implant 200 and/or the expandable framework 210 may include a plurality of anchor members 240 projecting radially outward from the expandable framework 210 and/or the plurality of interconnected struts in the expanded configuration. In some embodiments, each anchor member of the plurality of anchor members 240 may include at least one base portion 242 fixedly secured to the expandable framework 210 and/or the plurality of interconnected struts. In some embodiments, each anchor member of the plurality of anchor members 240 may include at least one base portion 242 directly and/or fixedly attached to and/or at the expandable framework 210 and/or the plurality of interconnected struts. In some embodiments, the plurality of anchor members 240 may be configured to engage with the lateral wall of the left atrial appendage. Other configurations are also contemplated. Additional details regarding the plurality of anchor members 240 is discussed below.

In some embodiments, the occlusive implant 200 may optionally include an occlusive element 220 connected to, disposed on, disposed over, disposed about, or covering at least a portion of the expandable framework 210 and/or the plurality of interconnected struts. In some embodiments, the occlusive element 220 may be connected to, disposed on, disposed over, disposed about, or cover at least a portion of an outer (or outwardly facing) surface of the expandable framework 210 and/or the plurality of interconnected struts. In some embodiments, the occlusive element 220 may be attached to the proximal hub and/or may be attached to the expandable framework 210 at the proximal hub. In some embodiments, the occlusive element 220 may extend radially outward from and/or may extend distally from the proximal hub. In some embodiments, the occlusive element 220 may be attached and/or secured to the expandable framework 210 at a plurality of discrete locations. In some embodiments, one of, some of, and/or all of the plurality of anchor members 240 may extend through an occlusive element 220, where present.

In some embodiments, the occlusive element 220 may include a membrane, a fabric, a mesh, a tissue element, or another suitable construction. In some embodiments, the occlusive element 220 may be porous. In some embodiments, the occlusive element 220 may be non-porous. In some embodiments, the occlusive element 220 may be permeable to selected gases and/or fluids. In some embodiments, the occlusive element 220 may be substantially impermeable to selected gases and/or fluids, such as blood, water, etc. In some embodiments, the occlusive element 220 may be designed, sized, and/or configured to prevent thrombus and/or embolic material from passing out of the left atrial appendage into the left atrium and/or the patient's bloodstream. In some embodiments, the occlusive element 220 may be configured to promote endothelization after implantation, thereby effectively removing the target site (e.g., the left atrial appendage, etc.) from the patient's circulatory system. Some suitable, but non-limiting, examples of materials for the occlusive element 220 are discussed below.

Figure 7:
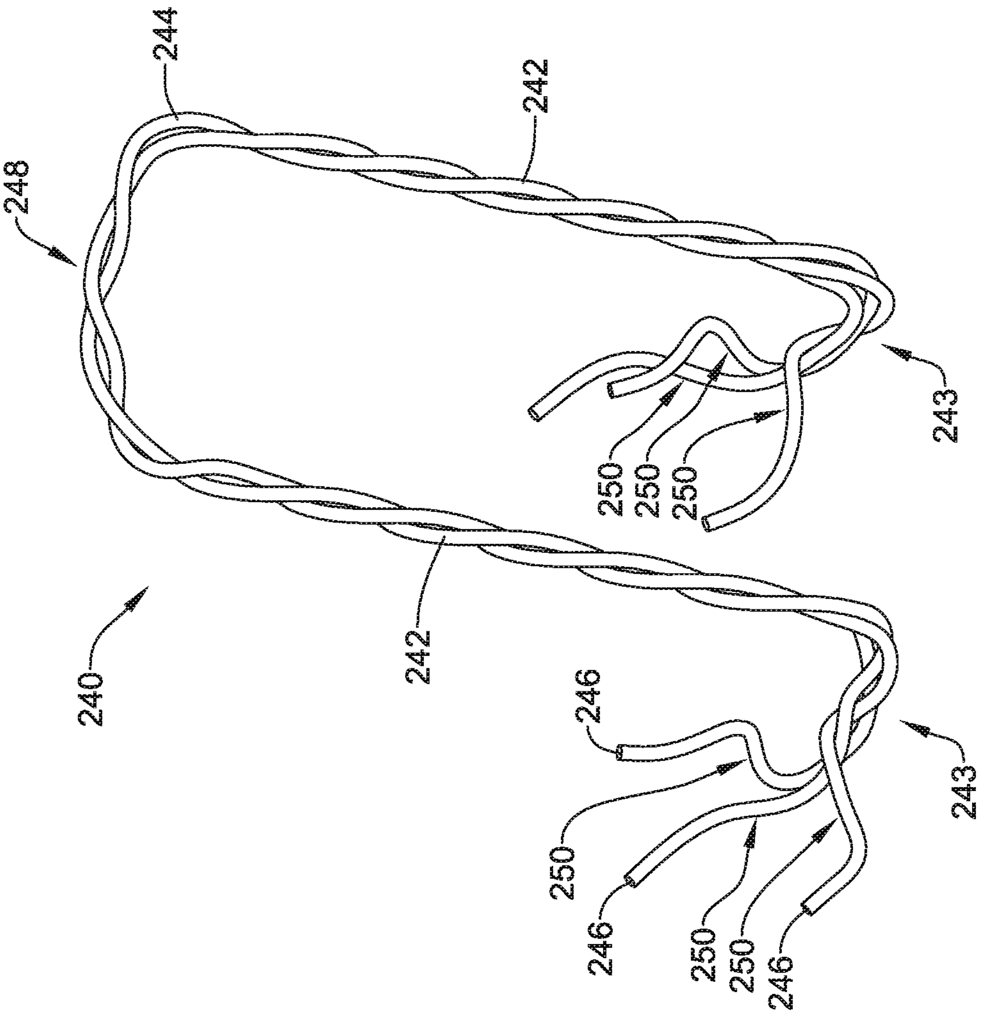
FIG. 7 is a perspective view illustrating an example anchor member according to the disclosure.

FIG. 7 illustrates an example embodiment of one of the plurality of anchor members 240 associated with the occlusive implant 200. As will be understood, the discussion herein related to the plurality of anchor members 240 may be applied equally to and/or may be used in place of each of the plurality of anchor members 240 present in the occlusive implant 200. References to the expandable framework 210 and/or elements thereof discussed herein, while not expressly shown, may be understood to be as discussed herein (with respect to FIGS. 4-6, for example).

As discussed herein, the expandable framework 210 may include a plurality of anchor members 240 extending radially outward from the expandable framework 210 in the expanded configuration. Each anchor member of the plurality of anchor members 240 may include at least one base portion 242 fixedly secured and/or fixedly attached to the expandable framework 210 and/or the plurality of interconnected struts. In some embodiments, each anchor member of the plurality of anchor members 240 is formed separately from the expandable framework 210 and later fixedly secured and/or fixedly attached to the expandable framework 210.

Each anchor member of the plurality of anchor members 240 may include a pedestal portion 243 and a plurality of anchor tips 246 extending from each base portion of the at least one base portion 242. In some embodiments, the pedestal portion 243 may be disposed between each base portion of the at least one base portion 242 and the plurality of anchor tips 246 extending from each base portion. In some embodiments, the pedestal portion 243 may extend outward from each base portion of the at least one base portion 242 and the plurality of anchor tips 246 may extend outward from the pedestal portion 243. In some embodiments, the pedestal portion 243 may be integrally and/or monolithically formed with the at least one base portion 242 and/or the plurality of anchor tips 246. Each anchor tip of the plurality of anchor tips 246 may be configured to penetrate tissue. In some embodiments, each anchor tip of the plurality of anchor tips 246 may include a rounded tip. In some embodiments, each anchor tip of the plurality of anchor tips 246 may include a flattened tip. In some embodiments, each anchor tip of the plurality of anchor tips 246 may include a sharpened tip. Other configurations, including various combinations thereof, are also contemplated.

Figure 8:
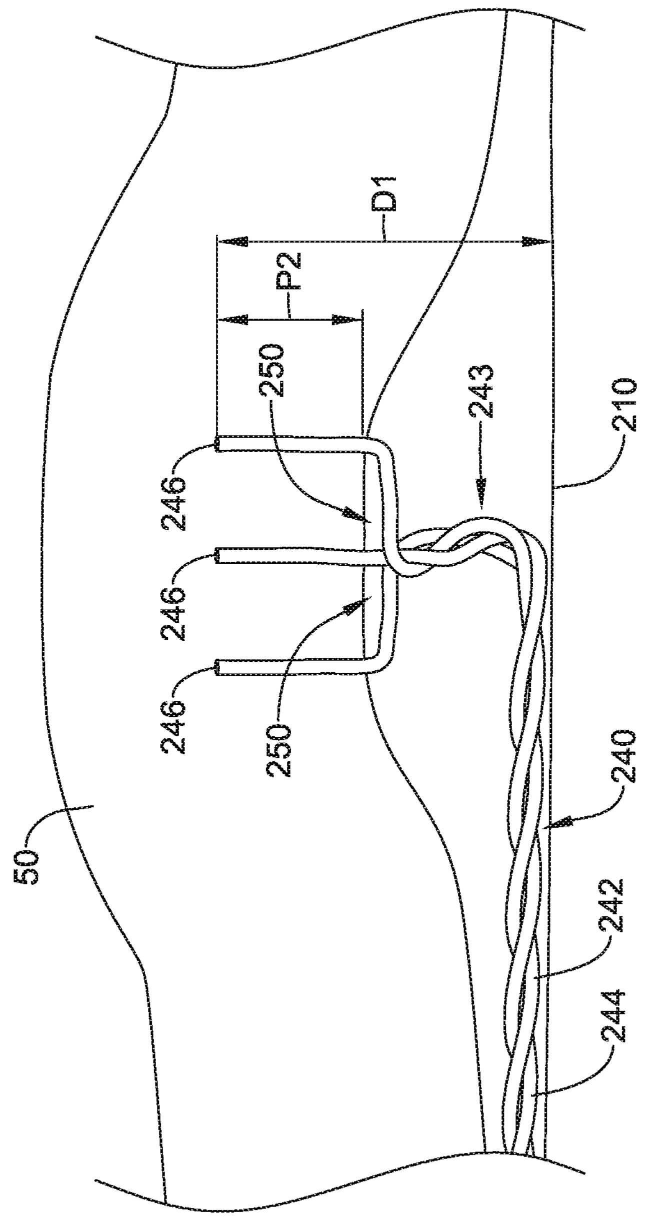
FIGS. 8-8A illustrate penetration of the example anchor member into tissue.
Figure 8A:
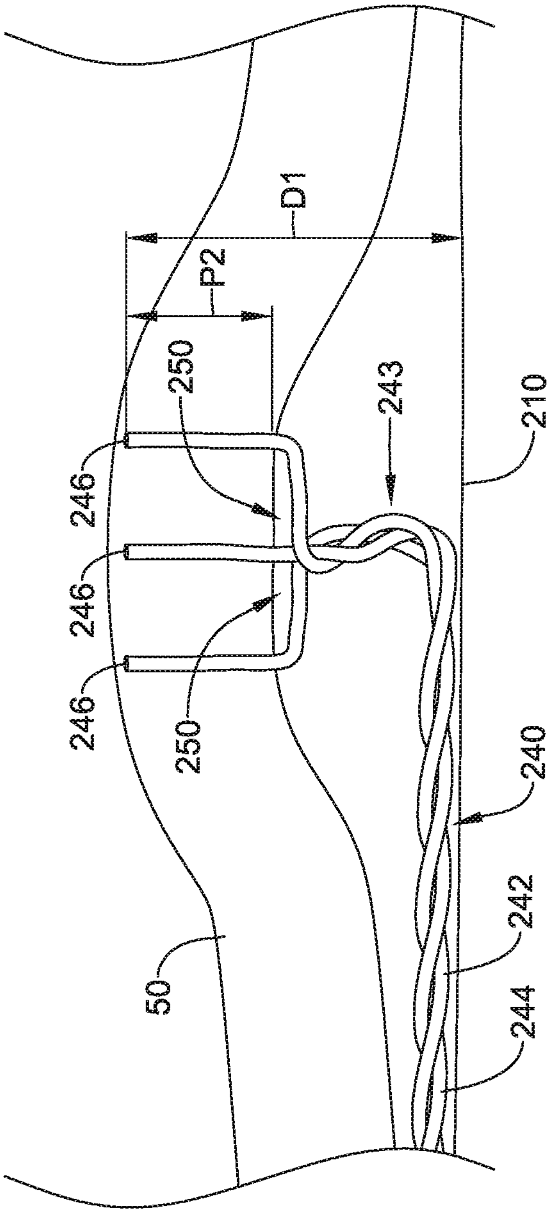
Figure 9:
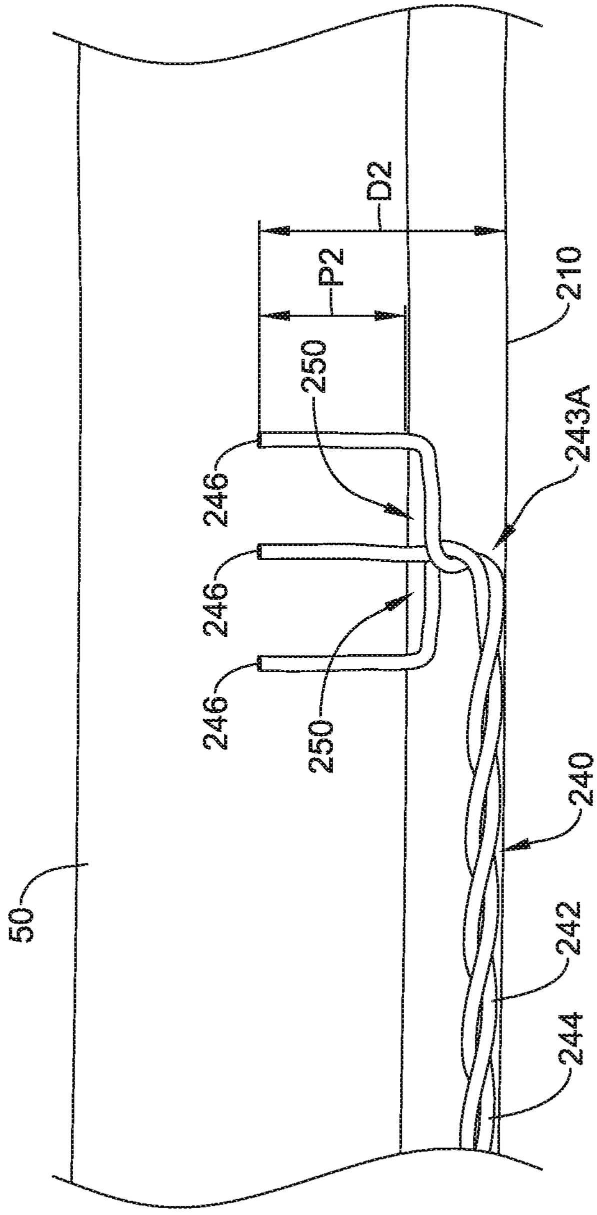
FIGS. 9-9A illustrate penetration of the example anchor member into tissue.
Figure 9A:
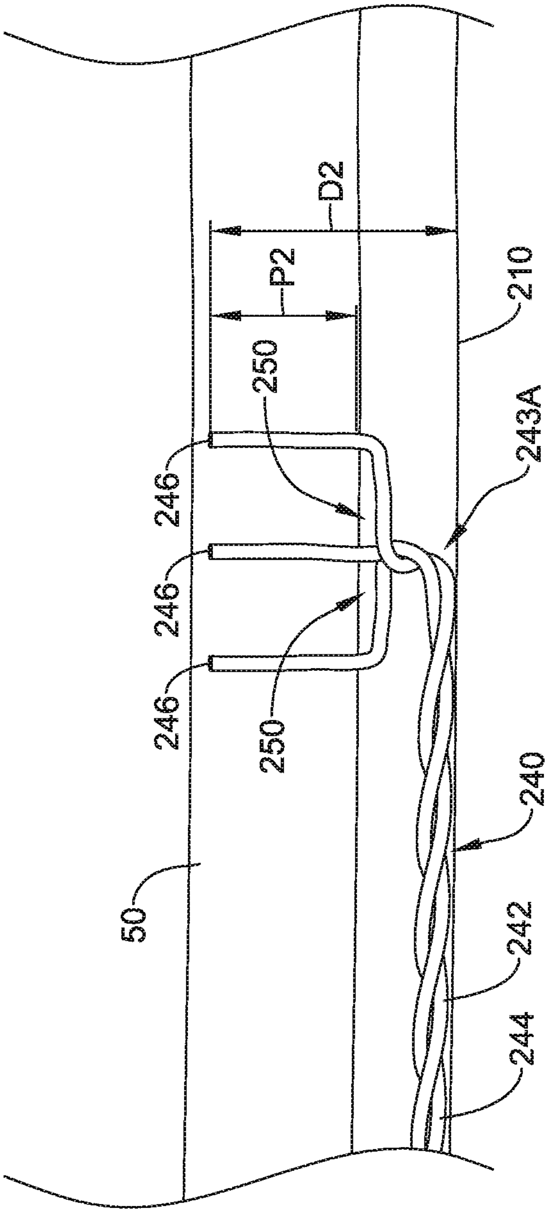

In some embodiments, the plurality of anchor tips 246 extending from each base portion of the at least one base portion 242 collectively form a tissue shelf 250 configured to limit the depth of penetration P2 of the plurality of anchor tips 246 into the tissue 50, as seen in FIGS. 8-9A, and the extension distance D1 of the outermost extent of the plurality of anchor tips 246 from the expandable framework 210 seen in FIGS. 8-8A. In an alternative configuration, the pedestal portion 243A may be configured to deflect and/or "lay down" against the expandable framework 210, such that the extension distance D2 of the outermost extent of the plurality of anchor tips 246 from the expandable framework 210 is reduced, as seen in FIGS. 9-9A.

In some embodiments, the tissue shelf 250 may be formed from a laterally extending portion of each of the plurality of anchor tips 246. For example, each of the plurality of anchor tips 246 may include a flattened portion oriented generally perpendicular to the pedestal portion 243 and/or a distalmost tip portion of each of the plurality of anchor tips 246. By providing the plurality of anchor tips 246 (e.g., more than the one wire barb 12/22 shown in FIG. 3) on each base member of the at least one base portion 242 and/or on each pedestal portion, anchoring is improved over a single wire barb while limiting penetration into the tissue 50 may improve the ability to reposition and/or recapture the occlusive implant 200 while limiting and/or without causing unnecessary and/or unintended damage to the tissue 50. Returning to FIGS. 8-8A, anchoring may be improved because the pedestal portion 243 "lifts" the tissue 50 relative to the expandable framework 210, thereby increasing engagement force between the plurality of anchor tips 246 and the tissue 50 and/or against the tissue shelf 250 which then transfers down the pedestal portion 243 to the at least one base portion 242 and the expandable framework 210.

In at least some embodiments, each base portion of the at least one base portion 242 may extend longitudinally along the expandable framework 210. Each base portion of the at least one base portion 242 may extend longitudinally along an outer surface of the expandable framework 210. In some embodiments, each base portion of the at least one base portion 242 may extend longitudinally along the expandable framework 210 toward a distal end of the expandable framework 210.

Returning to FIG. 7, in some embodiments, the at least one base portion 242 of each anchor member may include more than one base portion. In at least some embodiments, each anchor member of the plurality of anchor members 240 may include a bridge portion 248 connecting two base portions fixedly secured to the expandable framework 210 and a plurality of anchor tips 246 extending from each base portion of the two base portions. Each base portion of the two base portions may be fixedly secured to the expandable framework 210. While not expressly illustrated, in some embodiments, the at least one base portion 242 of each anchor member may include more than two base portions. In some embodiments, each anchor member of the plurality of anchor members 240 may include a bridge portion 248 connecting the more than two base portions. In some embodiments, the bridge portion 248 may be fixedly secured to the expandable framework 210 in addition to or in alternative to each base portion of the at least one base portion 242. Other configurations are also contemplated.

Each anchor member of the plurality of anchor members 240 may include and/or may be formed from at least two twisted filaments 244. In some embodiments, each of the at least two twisted filaments 244 forms one of the plurality of anchor tips 246. In some embodiments, each of the at least two twisted filaments 244 forms exactly one anchor tip of the plurality of anchor tips 246. For example, in some embodiments, each base portion of an anchor member having exactly two twisted filaments 244 will have exactly two anchor tips extending therefrom. Other configurations are also contemplated.

In some embodiments, the at least two twisted filaments 244 may form each base portion of the at least one base portion 242. For example, in embodiments of an anchor member having two base portions and the bridge portion 248, the at least two twisted filaments 244 form two base portions, the bridge portion 248 connecting the two base portions, and a plurality of anchor tips 246 extending from each base portion.

In some embodiments, forming the plurality of anchor members 240 may include twisting at least two filaments 244 together to form each anchor member, wherein each filament 244 has a first end and a second end. In some embodiments, forming the plurality of anchor members 240 may include separating and/or splaying apart the first ends of the at least two filaments 244 to form the plurality of anchor tips 246 of a first base portion of the at least one base portion 242 (and/or of the two base portions) and separating and/or splaying apart the second ends of the at least two filaments 244 to form the plurality of anchor tips 246 of a second base portion of the at least one base portion 242 (and/or of the two base portions), wherein portions of the at least two filaments 244 that remain twisted together form each base portion and the bridge portion 248 of each anchor member of the plurality of anchor members 240.

In some embodiments, each anchor member of the plurality of anchor members 240 may include and/or may be formed from at least three twisted filaments 244. In some embodiments, each of the at least three twisted filaments 244 forms one of the plurality of anchor tips 246. In some embodiments, each of the at least three twisted filaments 244 forms exactly one anchor tip of the plurality of anchor tips 246. For example, in some embodiments, each base portion of an anchor member having exactly three twisted filaments 244 will have exactly three anchor tips extending therefrom. Other configurations are also contemplated.

In some embodiments, the at least three twisted filaments 244 may form each base portion of the at least one base portion 242. For example, in embodiments of an anchor member having two base portions and the bridge portion 248, the at least three twisted filaments 244 form two base portions, the bridge portion 248 connecting the two base portions, and a plurality of anchor tips 246 extending from each base portion.

In some embodiments, forming the plurality of anchor members 240 may include twisting at least three filaments 244 together to form each anchor member, wherein each filament 244 has a first end and a second end. In some embodiments, forming the plurality of anchor members 240 may include separating and/or splaying apart the first ends of the at least three filaments 244 to form the plurality of anchor tips 246 of a first base portion of the at least one base portion 242 (and/or of the two base portions) and separating and/or splaying apart the second ends of the at least three filaments 244 to form the plurality of anchor tips 246 of a second base portion of the at least one base portion 242 (and/or of the two base portions), wherein portions of the at least three filaments 244 that remain twisted together form each base portion and the bridge portion 248 of each anchor member of the plurality of anchor members 240.

Figure 10:
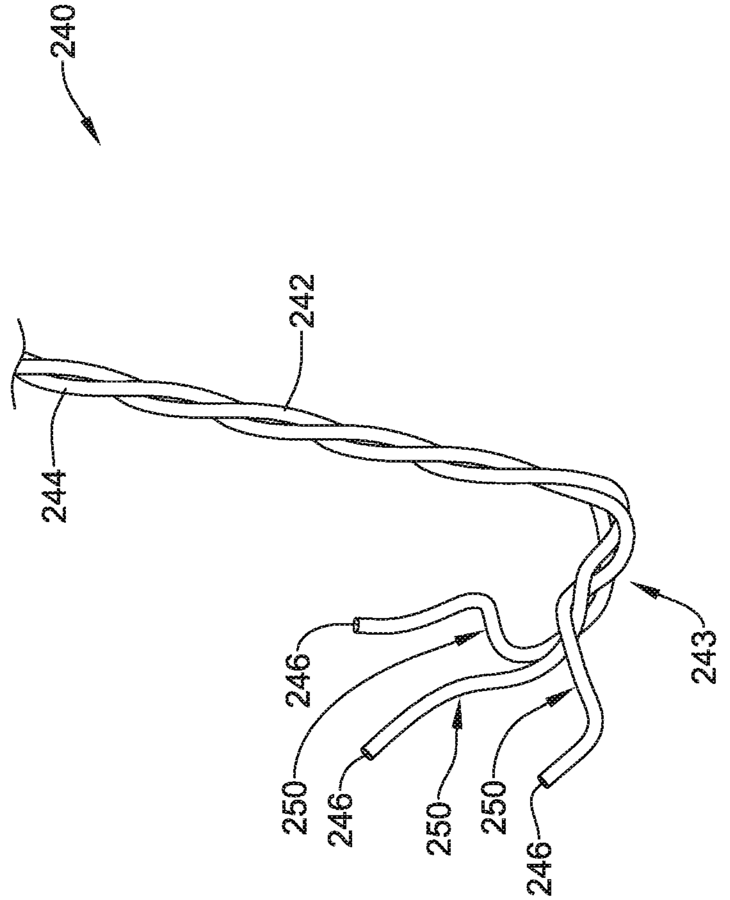
FIG. 10 is a perspective view illustrating an alternative configuration of an anchor member according to the disclosure.

FIG. 10 illustrates an alternative configuration of an anchor member of the plurality of anchor members 240. Similar to FIG. 7, each anchor member of the plurality of anchor members 240 may include at least one base portion 242 fixedly secured and/or fixedly attached to the expandable framework 210 and/or the plurality of interconnected struts. In some embodiments, each anchor member of the plurality of anchor members 240 is formed separately from the expandable framework 210 and later fixedly secured and/or fixedly attached to the expandable framework 210.

Each anchor member of the plurality of anchor members 240 may include a pedestal portion 243 and a plurality of anchor tips 246 extending from each base portion of the at least one base portion 242. In some embodiments, the pedestal portion 243 may extend from each base portion of the at least one base portion 242 and the plurality of anchor tips 246 may extend from the pedestal portion 243. Each anchor tip of the plurality of anchor tips 246 may be configured to penetrate tissue. In some embodiments, each anchor tip of the plurality of anchor tips 246 may include a rounded tip. In some embodiments, each anchor tip of the plurality of anchor tips 246 may include a flattened tip. In some embodiments, each anchor tip of the plurality of anchor tips 246 may include a sharpened tip. Other configurations, including various combinations thereof, are also contemplated.

In some embodiments, the plurality of anchor tips 246 extending from each base portion of the at least one base portion 242 collectively form a tissue shelf 250 configured to limit the depth of penetration P2 of the plurality of anchor tips 246 into the tissue 50 and the extension distance D1 of the outermost extent of the plurality of anchor tips 246 from the expandable framework 210 (e.g., FIGS. 8-8A). In some embodiments, the tissue shelf 250 may be formed from a laterally extending portion of each of the plurality of anchor tips 246. For example, each of the plurality of anchor tips 246 may include a flattened portion oriented generally perpendicular to the pedestal portion 243 and/or a distalmost tip portion of each of the plurality of anchor tips 246. By providing the plurality of anchor tips 246 (e.g., more than the one wire barb 12/22 shown in FIG. 3) on each base member of the at least one base portion 242 and/or on each pedestal portion, anchoring is improved over a single wire barb while limiting penetration into the tissue 50 may improve the ability to reposition and/or recapture the occlusive implant 200 while limiting and/or without causing unnecessary and/or unintended damage to the tissue 50. Similar to above (e.g., FIGS. 8-8A), anchoring may be improved because the pedestal portion 243 "lifts" the tissue 50 relative to the expandable framework 210, thereby increasing engagement force between the plurality of anchor tips 246 and the tissue 50 and/or against the tissue shelf 250 which then transfers down the pedestal portion 243 to the at least one base portion 242 and the expandable framework 210.

In at least some embodiments, each base portion of the at least one base portion 242 may extend longitudinally along the expandable framework 210. Each base portion of the at least one base portion 242 may extend longitudinally along an outer surface of the expandable framework 210. In some embodiments, each base portion of the at least one base portion 242 may extend longitudinally along the expandable framework 210 toward a distal end of the expandable framework 210. Returning to FIG. 10, in some embodiments, the at least one base portion 242 of each anchor member may include exactly one base portion.

Each anchor member of the plurality of anchor members 240 may include and/or may be formed from at least two twisted filaments 244. In some embodiments, each of the at least two twisted filaments 244 forms one of the plurality of anchor tips 246. In some embodiments, each of the at least two twisted filaments 244 forms exactly one anchor tip of the plurality of anchor tips 246. For example, in some embodiments, each base portion of an anchor member having exactly two twisted filaments 244 will have exactly two anchor tips extending therefrom. Other configurations are also contemplated.

In some embodiments, the at least two twisted filaments 244 may form each base portion of the at least one base portion 242. For example, in embodiments of an anchor member having exactly one base portion, the at least two twisted filaments 244 form exactly one base portion and a plurality of anchor tips 246 extending from the exactly one base portion.

In some embodiments, forming the plurality of anchor members 240 may include twisting at least two filaments 244 together to form each anchor member, wherein each filament 244 has a first end and a second end. In some embodiments, each base portion of the at least one base portion 242 is formed from twisting the first ends of the at least two filaments 244 together and the second ends of the at least two filaments 244 each form one of the plurality of anchor tips 246. For example, in some embodiments, forming the plurality of anchor members 240 may include separating and/or splaying apart the second ends of the at least two filaments 244 to form the plurality of anchor tips 246 of exactly one base portion, wherein the first ends and/or portions of the at least two filaments 244 that remain twisted together form the exactly one base portion of each anchor member of the plurality of anchor members 240.

In some embodiments, each anchor member of the plurality of anchor members 240 may include and/or may be formed from at least three twisted filaments 244. In some embodiments, each of the at least three twisted filaments 244 forms one of the plurality of anchor tips 246. In some embodiments, each of the at least three twisted filaments 244 forms exactly one anchor tip of the plurality of anchor tips 246. For example, in some embodiments, each base portion of an anchor member having exactly three twisted filaments 244 will have exactly three anchor tips extending therefrom. Other configurations are also contemplated.

In some embodiments, the at least three twisted filaments 244 may form each base portion of the at least one base portion 242. For example, in embodiments of an anchor member having exactly one base portion, the at least three twisted filaments 244 form exactly one base portion and a plurality of anchor tips 246 extending from the exactly one base portion.

In some embodiments, forming the plurality of anchor members 240 may include twisting at least three filaments 244 together to form each anchor member, wherein each filament 244 has a first end and a second end. In some embodiments, each base portion of the at least one base portion 242 is formed from twisting the first ends of the at least three filaments 244 together and the second ends of the at least three filaments 244 each form one of the plurality of anchor tips 246. For example, in some embodiments, forming the plurality of anchor members 240 may include separating and/or splaying apart the second ends of the at least three filaments 244 to form the plurality of anchor tips 246 of exactly one base portion, wherein the first ends and/or portions of the at least three filaments 244 that remain twisted together form the exactly one base portion of each anchor member of the plurality of anchor members 240.

In some embodiments, a method of making the occlusive implant 200 may include forming the expandable framework 210 having a central longitudinal axis extending from a proximal end to a distal end. The expandable framework 210 may be configured to shift between a collapsed configuration and an expanded configuration. In some embodiments, the expandable framework 210 may be biased toward and/or to the expanded configuration. In some embodiments, the expandable framework 210 may be self-biased toward and/or to the expanded configuration. In some embodiments, the expandable framework 210 may be mechanically expandable from the collapsed configuration toward and/or to the expanded configuration. In some embodiments, the expandable framework 210 may be balloon expandable from the collapsed configuration toward and/or to the expanded configuration. In some embodiments, the expandable framework 210 may be configured to self-expand from the collapsed configuration toward and/or to the expanded configuration. Other configurations are also contemplated.

The method may include forming a plurality of anchor members 240, wherein each anchor member includes at least one base portion 242 and a plurality of anchor tips 246 extending from each base portion of the at least one base portion 242. In some embodiments, each anchor member may include a pedestal portion 243 extending from each base portion of the at least one base portion 242 and a plurality of anchor tips 246 extending from the pedestal portion 243. In some embodiments, the pedestal portion 243 may be integrally and/or monolithically formed with the at least one base portion 242 and/or the plurality of anchor tips 246.

In some embodiments, the method and/or forming the plurality of anchor members 240 may include twisting at least two filaments 244 together to form each anchor member of the plurality of anchor members 240, wherein each filament 244 has a first end and a second end. In some embodiments, the method may include twisting at least two first filaments together to form a first anchor member including at least one base portion and a plurality of first anchor tips extending from each base portion of the first anchor member. In some embodiments, the method may include twisting at least two first filaments together to form a first anchor member including at least one base portion, a first pedestal portion, and a plurality of first anchor tips extending from the first pedestal portion. In some embodiments, the method may include twisting at least two second filaments together to form a second anchor member including at least one base portion and a plurality of second anchor tips extending from each base portion of the second anchor member. In some embodiments, the method may include twisting at least two second filaments together to form a second anchor member including at least one base portion, a second pedestal portion, and a plurality of second anchor tips extending from the second pedestal portion. Additional filaments may be twisted together to form additional anchor members as necessary. In some embodiments, each of the at least two first filaments and each of the at least two second filaments may be formed from a metallic material. In some embodiments, each of the at least two first filaments and each of the at least two second filaments may be formed from a polymeric material. Other configurations are also contemplated.

In some embodiments, the method and/or forming the plurality of anchor members 240 may include twisting at least three filaments 244 together to form each anchor member of the plurality of anchor members 240, wherein each filament 244 has a first end and a second end. In some embodiments, the method may include twisting at least three first filaments together to form a first anchor member including at least one base portion and a plurality of first anchor tips extending from each base portion of the first anchor member. In some embodiments, the method may include twisting at least three first filaments together to form a first anchor member including at least one base portion, a first pedestal portion, and a plurality of first anchor tips extending from the first pedestal portion. In some embodiments, the method may include twisting at least three second filaments together to form a second anchor member including at least one base portion and a plurality of second anchor tips extending from each base portion of the second anchor member. In some embodiments, the method may include twisting at least three second filaments together to form a second anchor member including at least one base portion, a second pedestal portion, and a plurality of second anchor tips extending from the second pedestal portion. Additional filaments may be twisted together to form additional anchor members as necessary. In some embodiments, each of the at least three first filaments and each of the at least three second filaments may be formed from a metallic material. In some embodiments, each of the at least three first filaments and each of the at least three second filaments may be formed from a polymeric material. Other configurations are also contemplated.

In some embodiments, the plurality of first anchor tips extending from each base portion of the at least one base portion and/or the first pedestal portion of the first anchor member may be spaced apart from each other in the expanded configuration. In some embodiments, the plurality of first anchor tips may collectively form a first tissue shelf configured to limit penetration of the plurality of first anchor tips into tissue. In some embodiments, the plurality of second anchor tips extending from each base portion of the at least one base portion and/or the second pedestal portion of the second anchor member may be spaced apart from each other in the expanded configuration. In some embodiments, the plurality of second anchor tips may collectively form a second tissue shelf configured to limit penetration of the plurality of second anchor tips into tissue. Additional anchor members, where present, may be configured in a similar manner.

In some embodiments, each base portion of the at least one base portion 242 and/or each pedestal portion may be fixedly secured together after twisting the at least two filaments 244 together to form each anchor member of the plurality of anchor members 240. In some embodiments, the at least two filaments 244 of each base portion of the at least one base portion 242 and/or of each pedestal portion may be welded, brazed, soldered, bonded, or otherwise fixedly attached to each other after twisting the at least two filaments 244 together to form each anchor member of the plurality of anchor members 240. In some embodiments, each base portion of the at least one base portion 242 and/or each pedestal portion may be fixedly secured together after twisting the at least three filaments 244 together to form each anchor member of the plurality of anchor members 240. In some embodiments, the at least three filaments 244 of each base portion of the at least one base portion 242 and/or of each pedestal portion may be welded, brazed, soldered, bonded, or otherwise fixedly attached to each other after twisting the at least three filaments 244 together to form each anchor member of the plurality of anchor members 240.

In some embodiments, the method may include fixedly attaching each anchor member of the plurality of anchor members 240 to the expandable framework 210. In some embodiments, the method may include fixedly attaching each base portion of the at least one base portion 242 to the expandable framework 210. In some embodiments, the method may include fixedly attaching each base portion of the at least one base portion 242 directly to the expandable framework 210. In some embodiments, each base portion of the at least one base portion 242 may be welded to the expandable framework 210. In some embodiments, each base portion of the at least one base portion 242 may be adhesively bonded to the expandable framework 210. In some embodiments, each base portion of the at least one base portion 242 may be brazed or soldered to the expandable framework 210. In some embodiments, each base portion of the at least one base portion 242 may be fixedly attached to the expandable framework 210 using mechanical fasteners. In some embodiments, each base portion of the at least one base portion may be integrally and/or monolithically formed with the expandable framework 210. In at least some embodiments, the pedestal portion 243 is not directly attached to and/or is not in direct contact with the expandable framework 210. Other configurations are also contemplated.

In some embodiments, the method may include fixedly attaching the first anchor member of the plurality of anchor members 240 and/or each base portion of the at least one base portion 242 of the first anchor member to the expandable framework 210. In some embodiments, the method may include fixedly attaching the first anchor member of the plurality of anchor members 240 and/or each base portion of the at least one base portion 242 of the first anchor member directly to the expandable framework 210. In some embodiments, the method may include fixedly attaching the first anchor member of the plurality of anchor members 240 and/or each base portion of the at least one base portion 242 of the first anchor member to the expandable framework 210 such that each base portion of the at least one base portion 242 of the first anchor member of the plurality of anchor members 240 extends longitudinally along the expandable framework 210 and/or is in direct contact with the expandable framework 210.

In some embodiments, the method may include fixedly attaching the second anchor member of the plurality of anchor members 240 and/or each base portion of the at least one base portion 242 of the second anchor member to the expandable framework 210. In some embodiments, the method may include fixedly attaching the second anchor member of the plurality of anchor members 240 and/or each base portion of the at least one base portion 242 of the second anchor member directly to the expandable framework 210. In some embodiments, the method may include fixedly attaching the second anchor member of the plurality of anchor members 240 and/or each base portion of the at least one base portion 242 of the second anchor member to the expandable framework 210 such that each base portion of the at least one base portion 242 of the second anchor member of the plurality of anchor members 240 extends longitudinally along the expandable framework 210 and/or is in direct contact with the expandable framework 210.

The materials that can be used for the various components of the system (and/or other elements disclosed herein) and the various components thereof disclosed herein may include those commonly associated with medical devices and/or systems. For simplicity purposes, the following discussion refers to the system. However, this is not intended to limit the devices and methods described herein, as the discussion may be applied to other elements, members, components, or devices disclosed herein, such as, but not limited to, the occlusive implant, the expandable framework, the occlusive element, the anchor member(s), etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable metals and metal alloys include stainless steel, such as 444V, 444L, and 314LV stainless steel; mild steel; nickel-titanium alloy such as linear elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super-elastic varieties, may exhibit distinct and useful mechanical properties. Linear elastic and/or non-super-elastic nitinol may be distinguished from super-elastic nitinol in that the linear elastic and/or non-super-elastic nitinol does not display a substantial "super-elastic plateau" or "flag region" in its stress/strain curve like super-elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super-elastic plateau and/or flag region that may be seen with super-elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super-elastic nitinol in that linear elastic and/or non-super-elastic nitinol may accept up to about 2-5% strain while remaining substantially elastic (e.g., before plastically deforming) whereas super-elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a super-elastic alloy, for example a super-elastic nitinol can be used to achieve desired properties.

In at least some embodiments, portions or all of the system and/or other elements disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the system and/or other elements disclosed herein. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system and/or other elements disclosed herein to achieve the same result.

In some embodiments, a degree of Magnetic Resonance Imaging (MRI) compatibility is imparted into the system and/or other elements disclosed herein. For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the system and/or other elements disclosed herein may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the system and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An occlusive implant, comprising:

an expandable framework having a central longitudinal axis extending from a proximal end to a distal end, the expandable framework being configured to shift between a collapsed configuration and an expanded configuration;

wherein the expandable framework includes a plurality of anchor members extending radially outward from the expandable framework in the expanded configuration, each anchor member of the plurality of anchor members comprising a plurality of filaments that are twisted together to form a twisted filaments assembly, each twisted filament assembly forming:

one or more base portions that are fixedly secured to the expandable framework;

a plurality of anchor tips extending from each of the one or more base portions, each of the plurality of anchor tips configured to penetrate tissue;

a tissue shelf formed by the plurality of anchor tips, the tissue shelf configured to limit how far each of the plurality of anchor tips penetrate the tissue;

wherein each of the one or more base portions extend longitudinally along the expandable framework.

2. The occlusive implant of claim 1, wherein the one or more base portions comprise a first base portion and a second portion.

3. The occlusive implant of claim 2, further comprising a bridge portion extending between the first base portion and the second base portion.

4. The occlusive implant of claim 1, wherein each twisted filament assembly comprises at least three twisted filaments.

5. The occlusive implant of claim 4, wherein each of the at least three twisted filaments forms one of the plurality of anchor tips.

6. The occlusive implant of claim 1, wherein each anchor tip of the plurality of anchor tops comprises a sharpened tip.

7. The occlusive implant of claim 1, wherein for each anchor member of the plurality of anchor members, each of the one or more base portions extend in a first direction.

8. The occlusive implant of claim 7, wherein each anchor member of the plurality of anchor members further comprise a pedestal portion in which the twisted filament assembly forming that anchor member bends in a second direction relative to the first direction.

* * * * *